(12) United States Patent
Sokol et al.

(10) Patent No.: US 11,596,657 B2
(45) Date of Patent: Mar. 7, 2023

(54) USE OF AHR AGONIST FOR THE PREVENTIVE OR CURATIVE TREATMENT OF METABOLIC SYNDROME AND THE ASSOCIATED DISORDERS

(71) Applicants: INSTITUT NATIONAL DE LA RECHERCHE AGRONOMIQUE, Paris (FR); SORBONNE UNIVERSITE, Paris (FR); ASSISTANCE PUBLIQUE—HOPITAUX DE PARIS, Paris (FR); INSTITUT NATIONAL DE LA SANTE ET DE LA RECHERCHE MEDICALE, Paris (FR)

(72) Inventors: Harry Sokol, Paris (FR); Jane Mea Natividad, Paris (FR); Bruno Lamas, Massy (FR); Henri Duboc, Versailles (FR); Mathias Lavie-Richard, Saint Cyr L'Ecole (FR); Marie-Laure Michel, Versailles (FR); Philippe Langella, Velizy (FR)

(73) Assignees: INSTITUT NATIONAL DE LA RECHERCHE AGRONOMIQUE, Paris (FR); SORBONNE UNIVERSITÉ, Paris (FR); ASSISTANCE PUBLIQUE—HÔPITAUX DE PARIS, Paris (FR); INSTITUT NATIONAL DE LA SANTE ET DE LA RECHERCHE MEDICALE, Paris (FR)

(*) Notice: Subject to any disclaimer, the term of this patent is extended or adjusted under 35 U.S.C. 154(b) by 12 days.

(21) Appl. No.: 16/337,951

(22) PCT Filed: Jul. 11, 2017

(86) PCT No.: PCT/EP2017/067438
§ 371 (c)(1),
(2) Date: Mar. 29, 2019

(87) PCT Pub. No.: WO2018/065132
PCT Pub. Date: Apr. 12, 2018

(65) Prior Publication Data
US 2019/0282638 A1 Sep. 19, 2019

(30) Foreign Application Priority Data
Oct. 4, 2016 (EP) .................................. 16306300

(51) Int. Cl.
| | | |
|---|---|---|
| A61K 35/747 | (2015.01) |
| A61P 1/16 | (2006.01) |
| A61P 3/04 | (2006.01) |
| A61P 3/10 | (2006.01) |
| A61K 35/745 | (2015.01) |
| A61K 35/744 | (2015.01) |
| A61K 31/138 | (2006.01) |
| A61K 31/167 | (2006.01) |
| A61K 31/40 | (2006.01) |
| A61K 31/42 | (2006.01) |
| A61K 31/44 | (2006.01) |
| A61K 36/258 | (2006.01) |
| A61K 31/404 | (2006.01) |
| A61K 31/4045 | (2006.01) |
| A61K 9/00 | (2006.01) |

(52) U.S. Cl.
CPC .......... *A61K 35/747* (2013.01); *A61K 31/138* (2013.01); *A61K 31/167* (2013.01); *A61K 31/40* (2013.01); *A61K 31/404* (2013.01); *A61K 31/4045* (2013.01); *A61K 31/42* (2013.01); *A61K 31/44* (2013.01); *A61K 35/744* (2013.01); *A61K 35/745* (2013.01); *A61K 36/258* (2013.01); *A61P 1/16* (2018.01); *A61P 3/04* (2018.01); *A61P 3/10* (2018.01); *A61K 9/0053* (2013.01); *Y02A 50/30* (2018.01)

(58) Field of Classification Search
CPC ... A61K 35/747; A61K 35/744; A61K 35/745
See application file for complete search history.

(56) References Cited

U.S. PATENT DOCUMENTS

| 10,238,697 B2 | 3/2019 | Langella et al. |
| 10,736,927 B2 | 8/2020 | Sokol et al. |

FOREIGN PATENT DOCUMENTS

| EP | 1 177 794 | 2/2002 |
| EP | 3031930 A1 * | 6/2016 | ........... A61K 35/747 |

OTHER PUBLICATIONS

Mallappa et al., "Management of metabolic syndrome through probiotic and prebiotic interventions", Indian J Endocrinol Metab. Jan.-Feb. 2012; 16(1): 20-27 (Year: 2012).*

Fak et al., "Lactobacillus reuteri Prevents Diet-Induced Obesity, but not Atherosclerosis, in a Strain Dependent Fashion in Apoe2/2 Mice", Oct. 2012 PLoS ONE 7(10):e46837; DOI: 10.1371/journal.pone.0046837 (Year: 2012).*

(Continued)

*Primary Examiner* — Ruth A Davis
(74) *Attorney, Agent, or Firm* — Saliwanchik, Lloyd & Eisenschenk

(57) ABSTRACT

The present invention relates to the preventive or curative treatment of metabolic syndrome and the associated disorders with AhR agonist or microorganism producing AhR agonist.

16 Claims, 24 Drawing Sheets
Specification includes a Sequence Listing.

(56) References Cited

OTHER PUBLICATIONS

Qi et al., "Lactobacillus maintains healthy gut mucosa by producing L-Ornithine", Communications Biology vol. 2, Article No. 171 (2019) (Year: 2019).*
Romani et al., "Microbiota control of a tryptophan-AhR pathway in disease tolerance to fungi", Eur. J. Immunology, 2014, 44:11, 3192-3200 (Year: 2014).*
U.S. Appl. No. 16/977,274, filed 2020.*
Averna et al. "Statins and metabolic syndrome", International Congress Series vol. 1253, Aug. 2003, pp. 243-246 (Year: 2003).*
Galleano et al. "Flavonoids and metabolic syndrome" Ann N Y Acad Sci. Jul. 2012;1259:87-94 (Year: 2012).*
Li et al. "Dietary Supplementation of Chinese Ginseng Prevents Obesity and Metabolic Syndrome in High-Fat Diet-Fed Mice", J Med Food. Dec. 1, 2014; 17(12): 1287-1297 (Year: 2014).*
Medjakovic, S et al. "Potential Health-modulating Effects of Isoflavones and Metabolites via Activation of PPAR and AhR" Nutrients, 2010, pp. 241-279, vol. 2, No. 3.
Bitto, A et al. "Effects of aglycone genistein in a rat experimental model of postmenopausal metabolic syndrome" Journal of Endocrinology, 2009, pp. 367-376, vol. 200, No. 3.
Bitto, A et al. "Genistein Aglycone a Nutraceutical Approach To Metabolic Syndrome: Results From a Randomized Clinical Trial in Postmenopausal Women" Atherosclerosis, 2014, EAS-0153, p. e109, vol. 235, No. 2, abstract only.
Wang, J et al. "Modulation of gut microbiota during probiotic-mediated attenuation of metabolic syndrome in high fat diet-fed mice" The ISME Journal, 2015, pp. 1-15, vol. 9, No. 1.
Cani, p. D et al. "Novel opportunities for next-generation probiotics targeting metabolic syndrome" Current Opinion in Biotechnology, 2015, pp. 21-27, vol. 32.
Anonymous, "Study of Danisco probiotics shows positive impact on metabolic syndrome (MetS)" Danisco, Apr. 19, 2010, XP-002676738, p. 1, retrieved from Internet: http://www.danisco.com/media/news/company_news/2010/study-of danisco probiotics shows positive_impact on metabolic_syndrome_mets/.
Takamura, T et al. "Lactobacillus bulgaricus OLL1181 activates the aryl hydrocarbon receptor pathway and inhibits colitis" Immunology and Cell Biology, 2011, pp. 817-822, vol. 89, No. 7.
Written Opinion in International Application No. PCT/EP2017/067438, Feb. 27, 2018, pp. 1-11.

* cited by examiner

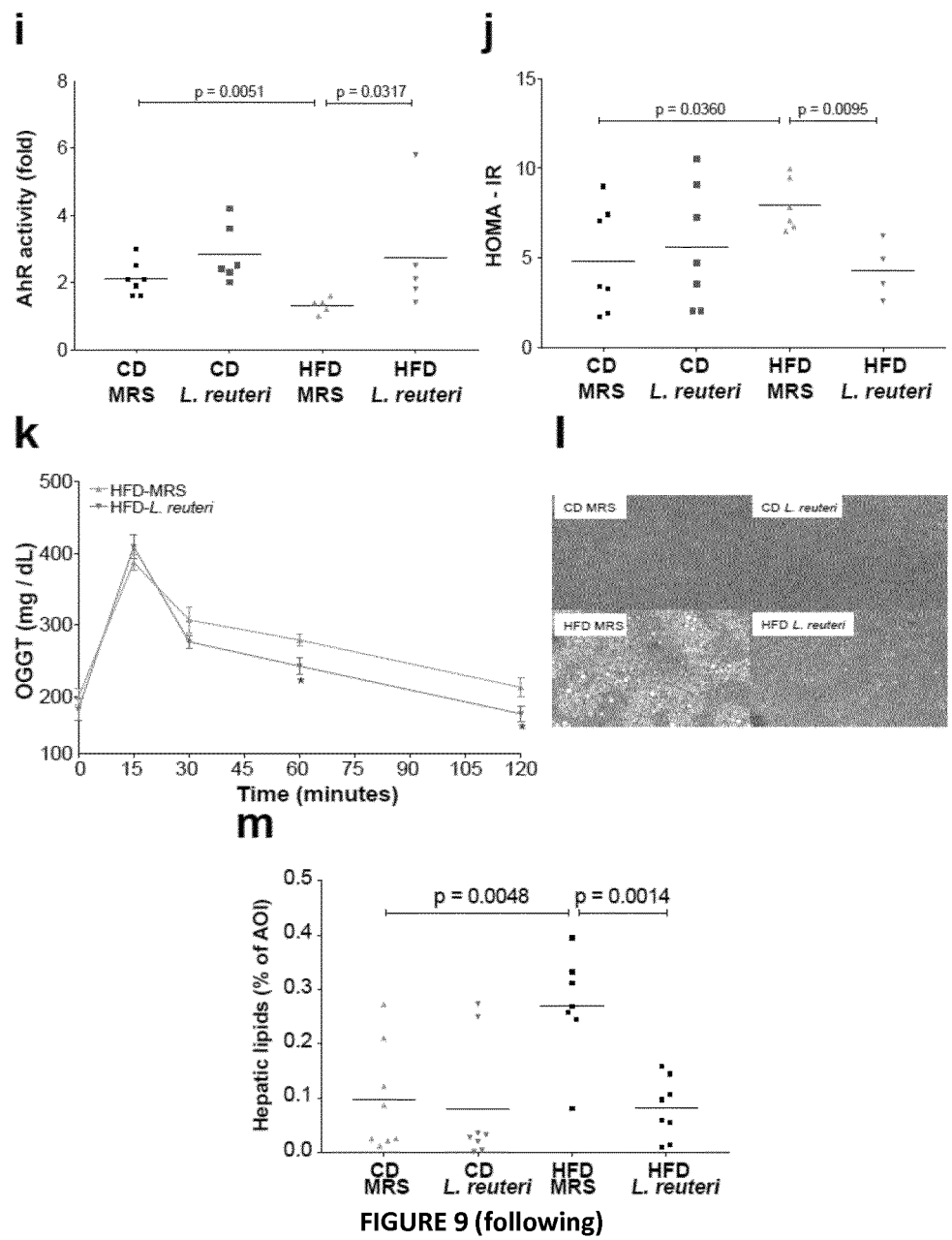
FIGURE 9 (following)

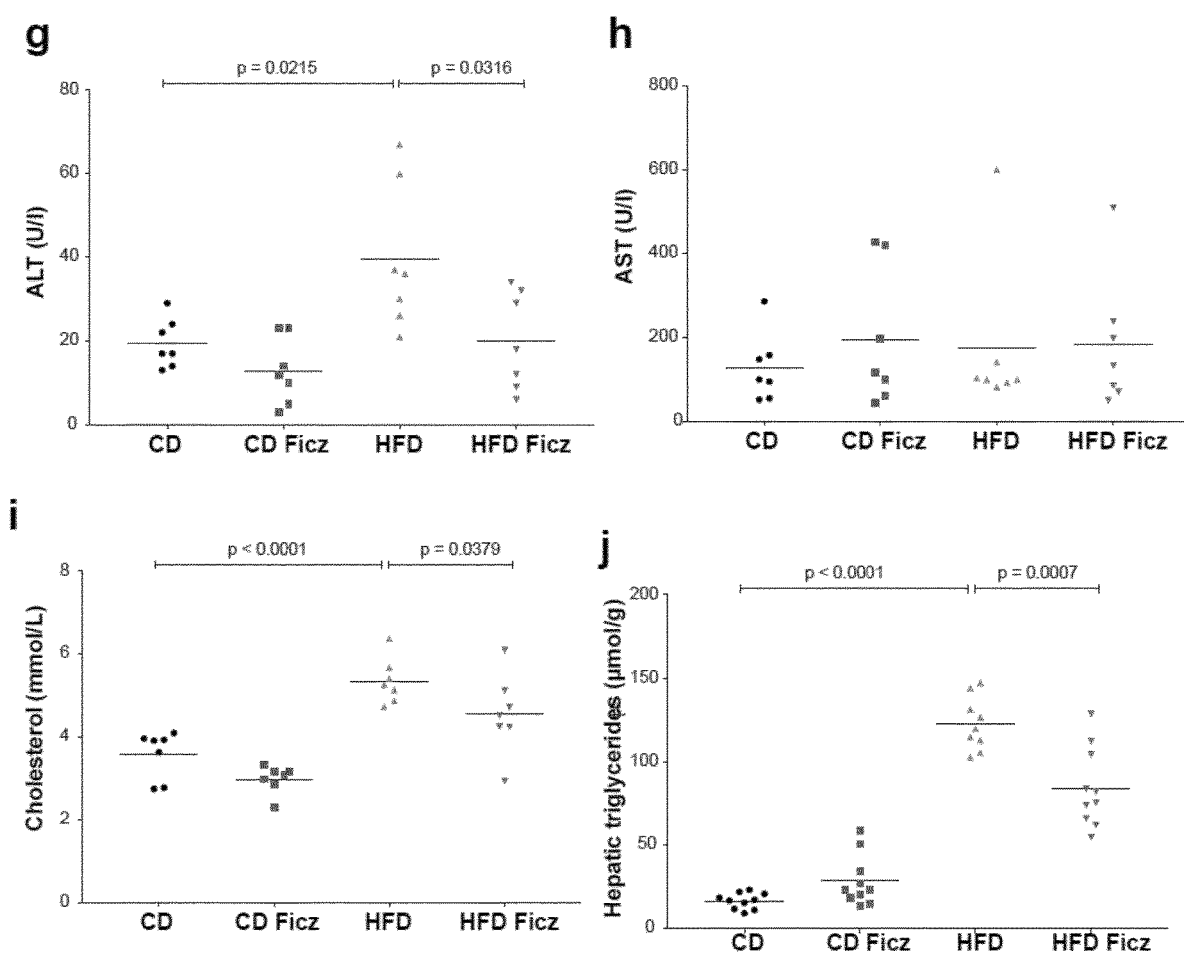
FIGURE 10 (following)

USE OF AHR AGONIST FOR THE PREVENTIVE OR CURATIVE TREATMENT OF METABOLIC SYNDROME AND THE ASSOCIATED DISORDERS

CROSS-REFERENCE TO RELATED APPLICATION

This application is the U.S. national stage application of International Patent Application No. PCT/EP2017/067438, filed Jul. 11, 2017.

The Sequence Listing for this application is labeled "Seq-List.txt" which was created on Feb. 28, 2019 and is 2 KB. The entire content of the sequence listing is incorporated herein by reference in its entirety.

FIELD OF THE INVENTION

The present invention relates to the field of medicine, in particular of the treatment of metabolic syndrome and the associated disorders.

BACKGROUND OF THE INVENTION

The metabolic syndrome is a cluster of the most dangerous heart attack and diabetes risk factors. This represents a major health problem because a quarter of the world's adults have metabolic syndrome. People with metabolic syndrome are twice as likely to die from, and three times as likely to have a heart attack or stroke compared with people without the syndrome. People with metabolic syndrome have a five-fold greater risk of developing type 2 diabetes.

Aryl-hydrocarbon receptor (AhR) is a ligand-activated nuclear receptor/transcription factor that regulates genes involved in toxicant metabolism and provides a major defense to environmental exposures. The AhR can be activated by dietary components such as fats and fat derivatives, and there is evidence linking the activated AhR to major diseases, including obesity (La Merill et al, 2009, Environ Health Perspect, 117, 1414-1419).

More recent publications suggest that AhR activity would be associated obesity and suggest that its inhibition would be beneficial against obesity.

Several studies have examined the AhR and fat metabolism using a model system comparing functional AhR signaling to one that is AhR deficient. Xu et al. (2015, Int J Obes, 39, 1300-1309) concluded that AhR deficiency protected against HFD (high Fat Diet)-induced obesity, hepatic steatosis, insulin resistance and inflammation, and preserved insulin signaling in major metabolic tissues. The authors suggested to target AhR for the development of pharmaceuticals, independent of food intake, to combat obesity and diabetes.

Kerley-Hamilton et al (2012, Environ Health Perspect, 120, 1252-1259) studied a model system with two different functional AhR, namely with high-affinity AhR and low-affinity AhR. They showed that mice with high-affinity AhR are more susceptible to obesity than mice with low-affinity AhR when fed Western diet. Therefore, the authors suggested to use of AhR antagonists for the treatment of obesity.

Park et al (2013, Biofactor, 39, 494-504) concluded that circulating AhR ligands may directly reduce mitochondrial function in tissues, leading to weight gain, glucose intolerance, and metabolic syndrome.

More recently, Moyer et al (2016, Toxicol Appl Pharmacol, 300:13-24) investigated into whether inhibition of the AHR prevents Western diet-based obesity and came to the conclusion that AHR antagonists α-naphthoflavone and CH-223191 significantly reduce obesity and adiposity and ameliorates liver steatosis in male C57Bl/6J mice fed a Western diet.

The metabolic syndrome remains a major issue for the health and it exists a strong need of any means suitable for fighting such a plague.

SUMMARY OF THE INVENTION

Surprisingly, the inventors observed that animal models of metabolic syndrome (high fat diet (HFD)-induced metabolic syndrome or leptin deficient mice (ob/ob mice)) are associated with a decreased AhR agonist activity of their gut microbiota and the administration of AhR agonist, either via a pharmacological strategy or a via an intestinal bacterium naturally producing AhR agonist, reduces the weight gain, and improves glucose tolerance, insulin sensitivity and fatty liver disease. In addition, they observed that, in human, the AhR agonist activity of the gut microbiota is inversely correlated with the metabolic syndrome.

Therefore, the present invention relates to a bacterial probiotic producing an aryl hydrocarbon receptor (AhR) agonist or an aryl hydrocarbon receptor (AhR) agonist for use for the preventive or curative treatment of metabolic syndrome and the associated disorders in a subject.

In particular, the associated disorders are selected from the group consisting of cardiovascular disease, in particular coronary heart disease, especially heart attack and stroke, insulin resistance, glucose intolerance, type 2 diabetes, fatty liver disease, in particular non-alcoholic fatty liver disease and non-alcoholic steatohepatitis, and lipodystrophy.

In one embodiment, the subject presents a decreased AhR activity, more particularly a decreased AhR activity of the gut microbiota.

In one embodiment, the AhR agonist can be selected, but is not limited to, from the group consisting of indoles derivatives, tryptophan catabolites of the microbiota, kynurenine, kynurenic acid, indole-3-aldehyde (IAld), tryptamine, indole 3-acetate, 3-indoxyl sulfate, 6-formylindolo (3,2-b)carbazole (FICZ), 2,3,7,8-tetrachlorodibenzo-p-dioxin (TCDD), tryptophan derivatives, flavonoids, biphenyls, AhR modulator (SAhRM), diindolylmethane (DIM), methyl-substituted diindolylmethanes, dihalo- and dialkylDIM analogs, mexiletine, polycyclic aromatic hydrocarbon (PAH), polychlorinated biphenyl (PCB), β-naphthoflavone (βNF), 5,6 benzoflavone (5,6 BZF), 3-indoxyl-sulfate (I3S),1-(4-Methylphenyl)-2-(4,5,6,7-tetrahydro-2-imino-3 (2H)-benzothiazolyl)ethanone hydrobromide (Pifithrin-α hydrobromide), (2'Z,3'E)-6-Bromo-1-methylindirubin-3'-oxime (MeB10), 5-hydroxy-7-methoxyflavone, 7-methoxyisoflavone, 6-methylflavone, 3-hydroxy-6-methylflavone, pinocembrin (5,7-dihydroxyflavanone) and 7,8,2'-trihydroxyflavone, 1,4-dihydroxy-2-naphthoic acid (DHNA), SU5416, CB7950998, Nimidipine, Flutamide, Atorvastatin, Leflunomide, *Ginseng* and natural AhR Agonists (NAhRAs).

In one embodiment, the bacterial probiotic producing an AhR agonist is a bacterium naturally producing an AhR agonist or a modified bacterium producing an AhR agonist, such as *Allobaculum* such as *Allobaculum stercoricanis*, *Lactobacillus* such as *Lactobacillus reuteri, Lactobacillus taiwanensis, Lactobacillus johnsonii, Lactobacillus animalis, Lactobacillus murinus, Lactobacillus salivarius, Lactobacillus gasseri, Lactobacillus bulgaricus,* and *Lactobacillus delbrueckii* subsp. *Bulgaricus,* the genus *Adlercreutzia,* the phylum Actinobacteria, lactic acid bacterium, *Strepto-*

*coccus thermophilus, Bifidobacterium*, Propionic acid bacterium, *Bacteroides, Eubacterium*, anaerobic *Streptococcus, Anaerostipes* such as *Anaerostipes hadrus, Anaerostipes caccae*, and *Anaerostipes butyraticus, Enterococcus, Ruminococcus gnavus, Faecalibacterium prausnitzii*, or *Escherichia coli*. In a preferred embodiment, the bacterial probiotic is an *Allobaculum*. In an alternative preferred embodiment, the bacterial probiotic is a *Lactobacillus*, preferably selected in the group consisting of *Lactobacillus reuteri, Lactobacillus taiwanensis, Lactobacillus animalis, Lactobacillus murinus, Lactobacillus salivarius, Lactobacillus gasseri, Lactobacillus bulgaricus*, and *Lactobacillus delbrueckii* subsp. *Bulgaricus*, more preferably of *Lactobacillus reuteri, Lactobacillus taiwanensis, Lactobacillus animalis, Lactobacillus murinus, Lactobacillus salivarius*, and *Lactobacillus gasseri*, still more preferably *Lactobacillus reuteri, Lactobacillus taiwanensis, Lactobacillus animalis*, and *Lactobacillus murinus*.

Preferably, the bacterial probiotic is selected from the group consisting of the strain CNCM I-5019, CNCM I-5020, CNCM I-5021, CNCM I-5022, CNCM I-5023, *Ruminococcus gnavus* ATCC29149, *Lactobacillus salivarius* DSM20555, *Lactobacillus reuteri* DSM20016, *Lactobacillus gasseri* DSM20243T, *Faecalibacterium prausnitzii* A2-165, *Escherichia coli* MG1665, *Anaerostipes hadrus* DSM3319, *Anaerostipes caccae* DSM14662, *Anaerostipes butyraticus* DSM22094, *Allobaculum stercoricanis* DSMZ13633 and combinations thereof. In a preferred embodiment, the bacterial probiotic is selected from the group consisting of bacterial probiotics available under CNCM deposit numbers CNCM I-5019, CNCM I-5020, CNCM I-5021, CNCM I-5022, CNCM I-5023 and any combination thereof. Alternatively, the bacterial probiotic is *Lactobacillus delbrueckii* subsp. *Bulgaricus*, in particular OLL1181 strain.

In one embodiment, the bacterial probiotic is to be administered by oral or rectal route. When an AhR agonist is used, the AhR agonist is to be administered by enteral or parenteral route, preferably be enteral route.

In addition, the present invention also relates to a bacterial probiotic selected from the group consisting of bacterial probiotics available under CNCM deposit numbers CNCM I-5019, CNCM I-5020, CNCM I-5021, CNCM I-5022, CNCM I-5023 and any combination thereof for use for the preventive or curative treatment of obesity.

DETAILED DESCRIPTION OF THE INVENTION

The inventors demonstrated that a metabolic syndrome induced by high fat diet (HFD) or genetically induced (ob/ob mice) leads to an impaired ability of the intestinal microbiota to produce AhR agonists. Correcting this defect by stimulation of AhR has a protective effect on weight gain, glycemic control, fatty liver disease and intestinal inflammation induced by HFD diet. These results are relevant for human as the same impaired ability of the microbiota to produce AhR agonists has been observed in obese patients and/or patients suffering from metabolic syndrome. Therefore, the stimulation of AhR could be an interesting preventive or curative treatment of metabolic syndrome and the associated disorders.

The invention relates to an AhR agonist or a bacterial probiotic producing an AhR agonist for use for the preventive or curative treatment of metabolic syndrome and the associated disorders. It also relates to the use of a bacterial probiotic producing an AhR agonist or an AhR agonist for the manufacture of a medicament for the preventive or curative treatment of metabolic syndrome and the associated disorders in a subject. It finally relates to a method for preventive or curative treatment of metabolic syndrome and the associated disorders in a subject comprising administering to the subject a bacterial probiotic producing an AhR agonist or an AhR agonist.

Metabolic Syndrome and Associated Disorders

The metabolic syndrome is defined by a clustering of at least three of the five following medical conditions:
Abdominal (central) obesity;
Elevated blood pressure;
Elevating fasting plasma glucose;
High serum triglycerides; and
Low high-density lipoprotein (HDL) levels.

It is important to note that obesity doesn't equate to metabolic syndrome. Patients who are of normal weight may also have the metabolic syndrome and, on the opposite, obese people may not have a metabolic syndrome. Indeed, as mentioned above, the metabolic syndrome is established if the obesity is an abdominal obesity and if at least two other medical conditions are observed.

According to the International Diabetes Federation, a consensus worldwide definition of the metabolic syndrome (2006) is: Central obesity (defined as waist circumference with ethnicity-specific values) and any two of the following: the abdominal (central) obesity:
Elevated blood pressure (BP): systolic BP >130 or diastolic BP >85 mm Hg, or treatment of previously diagnosed hypertension;
Elevating fasting plasma glucose (FPG): >100 mg/dL (5.6 mmol/L), or previously diagnosed type 2 diabetes;
High serum triglycerides refers to >150 mg/dL (1.7 mmol/L) or specific treatment for this lipid abnormality;
Low high-density lipoprotein (HDL) levels: <40 mg/dL (1.03 mmol/L) in males, <50 mg/dL (1.29 mmol/L) in females, or specific treatment for this lipid abnormality.

If BMI is >30 kg/m$^2$, central obesity can be assumed and waist circumference does not need to be measured.

Metabolic syndrome is associated with the risk of developing cardiovascular diseases, in particular coronary heart disease, especially heart attack and stroke, with insulin resistance, with glucose intolerance, with type 2 diabetes, with fatty liver disease, especially steatohepatitis, in particular non-alcoholic steatohepatitis, and with lipodystrophy.

In one particular embodiment, the metabolic syndrome is not a postmenopausal metabolic syndrome.

AhR

As used herein, the term "AhR" has its general meaning in the art and refers to Aryl hydrocarbon receptor, a transcription factor which is activated by diverse compounds and regulates the expression of xenobiotic metabolism genes. Aryl hydrocarbon receptor (AhR) is a member of the family of basic helix-loop-helix transcription factors, the bHLH-PAS (basic helix-loop-helix/Per-ARNT-Sim) family (Schmidt and Bradfield, 1996, Annu Rev Cell Dev Biol. 12, 55-89; Safe S et al. 2013, Toxicol Sci., 135, 1-16). It is described in the Uniprot database under P35869. The sequences of reference in Genbank are the followings: NM_001612.1 and NP 001621.4.

The term "AhR activity" has its general meaning in the art and refers to the biological activity associated with the activation of the AhR resulting from its signal transduction cascade, and including any of the downstream biological effects resulting from the binding of the candidate agent to AhR that may be equal or higher than the biological effect resulting from the binding of the AhR to its natural ligands.

Analyzing the AhR activation level may be assessed by any of a wide variety of well-known methods (Lehmann et al., 1995, Journal of Biological Chem., 270, 12953-12956; He et al., 2011, Environ Toxicol Chem, 30, 1915-1925; and Gao et al., 2009, Anal Biochem, 393, 163-175).

Subjects

The subject is a mammal, preferably a human being. In a particular embodiment, the subject is a man. In another particular embodiment, the subject is a woman. In a very particular embodiment, the subject is not a postmenopausal woman.

In on embodiment, the subject presents a decreased AhR activity, especially in a feces sample, more particularly a decreased AhR agonist activity of the gut microbiota.

In a particular embodiment, the activity of AhR is measured for the subject. Preferably, the AhR activity is the activity of the microbiota and is measured in a feces sample.

The present invention relates to a method of selecting a subject suffering of a metabolic syndrome for a treatment according to the present invention, wherein the subject presents a decreased AhR activity, especially in a feces sample. More particularly, the method comprises the steps of: i) determining the AhR agonist activity of the microbiota in a feces sample obtained from the subject, ii) comparing the level determined at step i) with a predetermined reference value, and iii) selecting the subject as suitable for the treatment when the level determined at step i) is lower than the predetermined reference value.

In one embodiment, the AhR activation level of the microbiota in a feces sample obtained from the subject is assessed by cell-based assays such as described in the example, He et al., 2011, supra and Gao et al., 2009, supra. The AhR activation level may be assessed by luciferase activity in AhR-responsive recombinant cells such as AhR-responsive recombinant guinea pig (G16L1.1c8), rat (H4L1.1c4), mouse (H1L1.1c2) and human (HG2L6.1c3) cells. The AhR activation level may also be assessed by measuring the ability to stimulate AhR-dependent gene expression using recombinant mouse hepatoma (Hepa1c1c7) cell-based CALUX (H1L1.1c2 and H1L6.1c2) clonal cell lines that contain a stably integrated AhR-/dioxin-responsive element (DRE)-driven firefly luciferase plasmid (pGudLuc1.1 or pGudLuc6.1, respectively) and CAFLUX (H1G1.1c3) clonal cell lines (He et al., 2011, supra). Typically, the AhR expression level is measured by performing the method described in the example.

In one embodiment, the AhR activation level of the microbiota in a feces sample obtained from the subject is assessed by measuring tryptophan metabolism. Accordingly, the AhR activation level may be assessed by measuring Tryptophan (Trp), kynurenine (Kyn) and indoles derivatives indole-3-acetic acid (IAA) concentrations (or other tryptophan metabolites), measuring Kyn/Trp, IAA/Trp and Kyn/IAA concentrations ratios.

In one embodiment, the AhR activation level is assessed using colon samples obtained from the subject by analyzing the expression of AhR target genes (such as interleukins IL-22 and IL-17), measuring IL-17$^+$ and IL-22$^+$ cells number, measuring AhR and chaperone proteins heterodimerization, measuring AhR nuclear translocation, or measuring AhR binding to its dimerization partner (AhR nuclear translocator (ARNT)).

As used herein, the "reference value" refers to a threshold value or a cut-off value. Typically, a "threshold value" or "cut-off value" can be determined experimentally, empirically, or theoretically. A threshold value can also be arbitrarily selected based upon the existing experimental and/or clinical conditions, as would be recognized by a person of ordinary skilled in the art. The threshold value has to be determined in order to obtain the optimal sensitivity and specificity according to the function of the test and the benefit/risk balance (clinical consequences of false positive and false negative). Typically, the optimal sensitivity and specificity (and so the threshold value) can be determined using a Receiver Operating Characteristic (ROC) curve based on experimental data. Preferably, the person skilled in the art may compare the AhR activation levels (obtained according to the method of the invention) with a defined threshold value. In one embodiment of the present invention, the threshold value is derived from the AhR activation level (or ratio, or score) determined in a feces sample derived from one or more healthy subjects, especially who are not suffering of a metabolic syndrome. Furthermore, retrospective measurement of the AhR activation level (or ratio, or scores) in properly banked historical subject samples may be used in establishing these threshold values.

In one embodiment, the subject to be treated has a High Fat diet or a high calorie diet and not a heart-healthy diet. For instance, the high fat diet provides more than 30% of energy as fat.

AhR Agonist

The term "AhR agonist" has its general meaning in the art and refers to a compound that selectively activates the AhR. The term "AhR agonist" refers to natural AhR ligands and any compound that can directly or indirectly stimulate the signal transduction cascade related to the AhR. As used herein, the term "selectively activates" refers to a compound that preferentially binds to and activates AhR with a greater affinity and potency, respectively, than its interaction with the other members of bHLH-PAS transcription factors family. Compounds that prefer AhR, but that may also activate other sub-types, as partial or full agonists are contemplated. Typically, an AhR agonist is a small organic molecule or a peptide.

Tests and assays for determining whether a compound is an AhR agonist are well known by the skilled person in the art such as described in Ji et al., 2015, Dig Dis Sci, 60, 1958-1966; Furumatsu et al., 2011, Dig Dis Sci, 56, 2532-2544; WO 2013/171696; WO 2012/015914; U.S. Pat. No. 6,432,692. In vitro and in vivo assays may be used to assess the potency and selectivity of the candidate agents to induce AhR activity.

Activities of the candidate agents, their ability to bind AhR and their ability to induce similar effects to those of indole derivatives such as indole-3-aldehyde (IAld) or 6-formylindolo(3,2-b)carbazole (FICZ), may be tested using isolated cells expressing AhR, AhR-responsive recombinant cells, colonic and small intestine lamina proporia cells expressing AhR, Th17/Th22 cells, γδT cells, NKp46$^+$ ILC cells, group 3 innate lymphoid cells (ILC3s) expressing the AhR, CHO cell line cloned and transfected in a stable manner by the human AhR or other tissues expressing AhR.

Activities of the candidate agents and their ability to bind to the AhR may be assessed by the determination of a Ki on the AhR cloned and transfected in a stable manner into a CHO cell line and measuring the expression of AhR target genes, measuring Trp, Kyn and indoles derivatives (IAA) concentrations, measuring Kyn/Trp, IAA/Trp and Kyn/IAA concentrations ratios, measuring IL-17$^+$ and IL-22$^+$ cells, measuring AhR and chaperone proteins heterodimerization, measuring AhR nuclear translocation, or measuring AhR binding to its dimerization partner (AhR nuclear translocator (ARNT)) in the present or absence of the candidate agent.

The AhR agonist activity can be for instance assess by the expression of one or more AhR target genes, such as the AhR repressor AHRR, and isozymes of the cytochrome P450 family 1 such as CYP1B1, CYP1A1 and CYP1A2.

Cells, intestine cells and other tissues expressing another receptor than AhR may be used to assess selectivity of the candidate agents.

The AhR agonists include synthetic and naturally occurring compounds.

In one embodiment of the invention, the agent which is an AhR agonist may be a molecule, or a mixture of agents such botanical extract, that directly interacts with the AhR protein. Preferably, it induces its dissociation from the chaperone proteins resulting in its translocation into the nucleus and dimerizing with ARNT (AhR nuclear translocator), and leads to changes in target genes transcription to produce a physiological effect. Reference to "ARNT" and "aryl hydrocarbon nuclear translocator" herein includes all mammalian versions of the protein and gene encoding the protein. In one aspect, ARNT is human ARNT.

Agonists of AhR include halogenated aromatic hydrocarbons (polychlorinated dibenzodioxins, dibenzofurans and biphenyls) and polycyclic aromatic hydrocarbons (3-methylcholanthrene, benzo-α-pyrene, benzanthracenes and benzoflavones). In particular, they include, but are not limited to, indoles derivatives, tryptophan catabolites such as tryptophan catabolites of the microbiota, kynurenine, kynurenic acid, indole-3-aldehyde (IAld), tryptamine, indole 3-acetate, 3-indoxyl sulfate, 6-formylindolo(3,2-b)carbazole (FICZ), indolo(3,2-b)carbazole (ICZ), 2-(1'H-indole-3'-carbonyl)-thiazole-4-carboxylic acid methyl ester (ITE), its precursor 2-(1'H-indole-3'-carbonyl)-thiazole-4-carboxylate (ITC) and analogs thereof disclosed in U.S. Pat. No. 7,419,992, 2,3,7,8-tetrachlorodibenzo-p-dioxin (TCDD), polycyclic aromatic hydrocarbon (PAH), polychlorinated biphenyl (PCB), beta-naphthoflavone (BNF), 3-indoxyl-sulfate (13S), 1-(4-Methylphenyl)-2-(4,5,6,7-tetrahydro-2-imino-3(2H)-benzothiazolyl)ethanone hydrobromide (Pifithrin-α hydrobromide), (2'Z,3'E)-6-Bromo-1-methylindirubin-3'-oxime (MeBIO), tryptophan derivatives, flavonoids and biphenyls, and the mixtures thereof.

Naturally occurring compounds that have been identified as ligands of AhR include derivatives of tryptophan such as indigo dye and indirubin, tetrapyrroles such as bilirubin, the arachidonic acid metabolites lipoxin-A4 and prostaglandin G, modified low-density lipoprotein and several dietary carotinoids (Denison et al., 2002, Chem. Biol. Interact. 141, 3-24; Denison et al., 2003, Annu. Rev. Pharmacol. Toxicol. 43, 309-334; Adachi J et al., 2001, J. Biol. Chem., 276, 31475-1478; Sinal C J and Bend J R, 1997, Mol. Pharmacol., 52, 590-9; Seidel S D, et al., 2001, J. Biochem. Mol. Toxicol., 15, 187-196; McMillan B J and Bradfield C A, 2007, Proc. Natl. Acad. Sci. U.S.A., 104, 1412-1417; Stevens et al., 2009, Immunology., 127, 299-311).

AhR agonists are as disclosed in Bisson et al., 2009, J. Med. Chem, 52, 5635-5641, for example, 5-hydroxy-7-methoxyflavone, 7-methoxyisoflavone, 6-methylflavone, 3-hydroxy-6-methylflavone, pinocembrin (5,7-dihydroxyflavanone) and 7,8,2'-trihydroxyflavone.

Other examples of AhR agonists are compound VAF347 [4-(3-chlorophenyl)-N-[4-(trifluoromethyl)phenyl]pyrimidin-2-amine], and its pro-drug version VAG539 [4-(3-chloro-phenyl)-pyrimidin-2-yl]-(4-trifluoromethyl-phenyl)-carbamic acid 2-[(2-hydroxy-ethyl)-methyl-amino]-ethyl ester] (Lawrence B P, 2008, Blood, 112, 1158-1165).

Another example is Semaxanib (SU5416) [3-(3,5-dimethyl-1H-pyrrol-2-ylmethylene)-1,3-dihydro-indole-2-one].

SU5416 was initially characterized as a potent and selective synthetic inhibitor of VEGF receptor/pathway, but was shown to be an AhR agonist that activates the human AhR with a potency approaching TCDD (Mezrich J D, et al. (2012) PLoS ONE 7(9): e44547).

In one embodiment, the compound which is a AhR agonist may be a selective AhR modulator (SAhRM) such as diindolylmethane (DIM), methyl-substituted diindolylmethanes, dihalo- and dialkylDIM analogs, mexiletine, β-naphthoflavone (3NF) (5,6 benzoflavone (5,6 BZF) and moieties described, for example, in Safe et al., 2013, Toxicol Sci., 135, 1-16; Furumatsu et al., 2011, Dig Dis Sci, 56, 2532-2544; and WO 2012/015914.

An AhR agonist also includes compounds described in WO 2012/015914 such as CB7950998.

An AhR agonist also includes natural extracts or fractions which are activators of the AhR pathway such as 1,4-dihydroxy-2-naphthoic acid (DHNA) and natural AhR Agonists (NAhRAs) disclosed in WO 2013/171696 and WO 2009/093207.

In a preferred embodiment, the AhR agonist is selected from a group of approved drugs having an agonist effect on AhR and consisting of Mexiletine, Nimidipine, Flutamide, Atorvastatin, Leflunomide, and *Ginseng* (Hu W et al, 2007, Mol Pharmacol., 71, 1475-86, O'Donnell E F, et al, 2010, PLoS One, 5(10). pii: e13128; Wang Y, et al, 2008, Eur J Pharmacol., 601, 73-78).

In one embodiment, the AhR agonists of the present invention excludes 2-(1'H-indole-3'-carbonyl)-thiazole-4-carboxylic acid methyl ester (ITE), its precursor 2-(1'H-indole-3'-carbonyl)-thiazole-4-carboxylate (ITC) and analogs thereof disclosed in U.S. Pat. No. 7,419,992. In another embodiment, the AhR agonists of the present invention excludes the AhR agonists having an effect on the angiogenesis or the use of such agonists in an amount having an effect on the angiogenesis.

Microorganism Producing AhR Agonist

In one embodiment, the agent of the present invention is a bacterial probiotic exhibiting AhR activation properties.

The term "bacterial probiotic" has its general meaning in the art and refers to a useful microorganism that improves the bacterial flora in the gastrointestinal tract and can bring a beneficial action to the host, and a growth-promoting substance therefor. The term "bacterial probiotic" also refers to a bacterium forming the bacterial flora and a substance that promotes the growth of such a bacterium. The term "bacterial probiotic" also refers to a useful microorganism that can bring a beneficial action to a host and substance produced by these microorganisms (microorganism culture). The term "bacterial probiotic" also refers to a dead microbial body and a microbial secretory substance. Because of a suitable enteric environment being formed and the action being independent of differences in enteric environment between individuals, the probiotic is preferably a living microbe.

The term "bacterial probiotic exhibiting AhR activation properties" has its general meaning in the art and relates to a probiotic which can activate the AhR. The term "bacterial probiotic exhibiting AhR activation properties" also relates to a probiotic capable of activating the AhR or having AhR activating potency. The term "AhR activation properties" means potency in being able to activate a signaling pathway that is initiated by AhR activation, and may involve any kind of activating mechanism. Therefore, it is not always necessary for a microbial body itself to be an AhR ligand, and for example a secretory substance produced by a microbe may have AhR-activating potency, or the AhR may be activated by a dead microbial body or homogenate thereof. A growth-promoting substance having AhR-activating potency includes a case in which the substance itself has AhR-activating potency and also a case in which the substance itself does not have AhR-activating potency but it promotes growth of a bacterium having AhR-activating potency. Therefore, when a "microorganism" or "bacterium" is referred to or a specific microbe is referred to in the present invention, they include not only a living microbe but also a dead microbial body or homogenate thereof and a culture of said microbe or a secretory substance. However, it is preferably a microbial body itself such as a living microbe or a dead microbial body or homogenate thereof, and from the viewpoint of being capable of forming bacterial flora in the gastrointestinal tract, it is more preferably a living microbe (US 2013/0302844).

Bacterial probiotics include, but are not limited to, bacterium exhibiting naturally AhR activation properties or modified bacterium exhibiting AhR activation properties such as *Allobaculum*, *Lactobacillus reuteri*, *Lactobacillus taiwanensis*, *Lactobacillus johnsonii*, *Lactobacillus animalis*, *Lactobacillus murinus*, the genus *Adlercreutzia*, the phylum Actinobacteria, lactic acid bacterium, *Lactobacillus bulgaricus*, *Streptococcus thermophilus*, *Bifidobacterium*, Propionic acid bacterium, *Bacteroides*, *Eubacterium*, anaerobic *Streptococcus*, *Enterococcus*, *Lactobacillus delbrueckii* subsp. *Bulgaricus*, *Escherichia coli*, other intestinal microorganisms and probiotics described for example in US 2013/0302844.

In a preferred embodiment, the bacterial probiotic is an *Allobaculum*. In an alternative preferred embodiment, the bacterial probiotic is a *Lactobacillus*, preferably selected in the group consisting of *Lactobacillus reuteri*, *Lactobacillus taiwanensis*, *Lactobacillus animalis*, and *Lactobacillus murinus*.

In particular, the inventors have isolated bacterial probiotics exhibiting AhR activation properties and have deposited them at the Collection Nationale de Cultures de Microorganismes (CNCM, Institut Pasteur, 25 rue du Docteur Roux, 75724 Paris Cedex 15, France), in accordance with the terms of Budapest Treaty. More particularly, 5 bacterial probiotics have been deposited on Sep. 30, 2015, at the CNCM with the deposit numbers CNCM I-5019 (SB6WTD3, *Lactobacillus taiwanensis*), CNCM I-5020 (SB6WTD4, *Lactobacillus murinus*), CNCM I-5021 (SB6WTD5, *Lactobacillus animalis*), CNCM I-5022 (SB6WTF6, *Lactobacillus reuteri*), and CNCM I-5023 (SB6WTG6, *Lactobacillus reuteri*). Accordingly, in a preferred embodiment, the bacterial probiotic exhibiting AhR activation properties is selected from the group consisting of the strain CNCM I-5019, CNCM I-5020, CNCM I-5021, CNCM I-5022, and CNCM I-5023, and combinations thereof.

In a preferred embodiment, the bacterial probiotic is capable of producing an AhR agonist. Bacterial probiotics include, but are not limited to, bacterium naturally producing an AhR agonist or modified bacterium producing an AhR agonist. Such bacterial probiotic can be selected from the group consisting of *Allobaculum* such as *Allobaculum stercoricanis*, *Lactobacillus* such as *Lactobacillus reuteri*, *Lactobacillus taiwanensis*, *Lactobacillus johnsonii*, *Lactobacillus animalis*, *Lactobacillus murinus*, *Lactobacillus salivarius*, *Lactobacillus gasseri*, *Lactobacillus bulgaricus*, and *Lactobacillus delbrueckii* subsp. *Bulgaricus*, the genus *Adlercreutzia*, the phylum Actinobacteria, lactic acid bacterium, *Streptococcus thermophilus*, *Bifidobacterium*, Propionic acid bacterium, *Bacteroides*, *Eubacterium*, anaerobic *Streptococcus*, *Anaerostipes* such as *Anaerostipes hadrus*, *Anaerostipes caccae*, and *Anaerostipes butyraticus*, *Enterococcus*, *Ruminococcus gnavus*, *Faecalibacterium prausnitzii*, *Escherichia coli*, other intestinal microorganisms and probiotics described for example in US 2013/0302844. In one embodiment, such bacterial probiotics include, but are not limited to, bacterium naturally producing an AhR agonist or modified bacterium producing an AhR agonist. Bacterial probiotic can be selected from the group consisting of *Allobaculum* such as *Allobaculum stercoricanis*, *Lactobacillus* such as *Lactobacillus reuteri*, *Lactobacillus taiwanensis*, *Lactobacillus animalis*, *Lactobacillus murinus*, *Lactobacillus salivarius*, *Lactobacillus gasseri*, *Anaerostipes* such as *Anaerostipes hadrus*, *Anaerostipes caccae*, and *Anaerostipes butyraticus*, *Ruminococcus* such as *Ruminococcus gnavus*, *Faecalibacterium* such as *Faecalibacterium prausnitzii*, and Enterobacteriaceae such as *Escherichia coli*. More specifically, such bacterial probiotic can be selected from the group consisting of the strain CNCM I-5019, CNCM I-5020, CNCM I-5021, CNCM I-5022, CNCM I-5023, *Ruminococcus gnavus* ATCC29149, *Lactobacillus salivarius* DSM20555, *Lactobacillus reuteri* DSM20016, *Lactobacillus gasseri* DSM20243T, *Faecalibacterium prausnitzii* A2-165, *Escherichia coli* MG1665, *Anaerostipes hadrus* DSM3319, *Anaerostipes caccae* DSM14662, *Anaerostipes butyraticus* DSM22094, *Allobaculum stercoricanis* DSMZ13633 and combinations thereof. In a particular embodiment, bacterial probiotic can be selected from the group consisting of the strain CNCM I-5019, CNCM I-5020, CNCM I-5021, CNCM I-5022, CNCM I-5023, and combinations thereof. The bacteria have been shown to produce AhR agonists (FIG. 19).

For instance, the patent application WO2015/025259 describes a bacterium producing indole-3-aldehyde.

The patent application US 2013/302844 also provides bacterial probiotics having AhR activating potency. The probiotics is selected from the group consisting of a Lactic acid bacterium, a *Bifidobacterium*, and a Propionic acid bacterium. Preferably, the probiotics is *Lactobacillus delbrueckii* subsp. *bulgaricus* OLL1181 strain (deposited on Jul. 16, 2010, with the International Patent Organism Depository, National Institute of Advanced Industrial Science and Technology (Chuo No. 6,1-1-1 Azuma, Tsukuba city, Ibaraki prefecture, Japan 305-8566) with depository number: FERM BP-11269).

The AhR activation level by the bacterial probiotic exhibiting AhR activation properties or by the bacterial probiotic producing an AhR agonist can be assessed by cell-based assays such as described in the example, He et al., 2011, supra and Gao et al., 2009, supra. The AhR activation level may be assessed by luciferase activity in AhR-responsive recombinant cells such as AhR-responsive recombinant guinea pig (G16L1.1c8), rat (H4L1.1c4), mouse (H1L1.1c2) and human (HG2L6.1c3) cells. The AhR activation level may also be assessed by measuring the ability to stimulate AhR-dependent gene expression using recombinant mouse hepatoma (Hepa1c1c7) cell-based CALUX (H1L1.1c2 and H1L6.1c2) clonal cell lines that contain a stably integrated AhR-/dioxin-responsive element (DRE)-driven firefly luciferase plasmid (pGudLuc1.1 or pGudLuc6.1, respectively) and CAFLUX (H1G1.1c3) clonal cell lines (He et al., 2011, supra). Typically, the AhR activation level is measured by performing the method described in the example, in particular in example 3. If the AhR agonist activity is measured by the method of example 3, the AhR fold change is at least 2, preferably at least 4.

In a particular embodiment, the present invention specifically relates to a bacterial probiotic selected from the group consisting of the strain CNCM I-5019, CNCM I-5020, CNCM I-5021, CNCM I-5022, and CNCM I-5023, and a combination thereof for use for the curative or preventive treatment of obesity. It further relates to a method for curative or preventive treatment of obesity of a subject, comprising administering a therapeutic effective amount of a bacterial probiotic selected from the group consisting of the strain CNCM I-5019, CNCM I-5020, CNCM I-5021, CNCM I-5022, and CNCM I-5023, and a combination thereof to the subject. Finally, it relates to the use of a bacterial probiotic selected from the group consisting of the strain CNCM I-5019, CNCM I-5020, CNCM I-5021, CNCM I-5022, and CNCM I-5023, and a combination thereof for the manufacture of a medicament for use for the curative or preventive treatment of obesity. The subject is an obese having a body mass index (BMI) higher than 30, preferably higher than 35, more preferably higher than 40, still more preferably from 40 to 50.

Optionally, the AhR agonist or bacterial probiotic exhibiting aryl hydrocarbon receptor (AhR) activation, in particular bacterial probiotic an AhR agonist, can be used in combination with an additional active ingredient.

When a bacterial probiotic is used in the treatment, it can be used in combination with other probiotics.

Pharmaceutical Composition and Administration

When the bacterial probiotics exhibiting AhR activation properties, in particular a bacterial probiotic producing an AhR agonist, is used for the treatment of the invention, the preferred administration route is oral or rectal, preferable oral route. Accordingly, in one embodiment, an oral composition comprising the bacterial probiotic exhibiting AhR activation properties, in particular a bacterial probiotic producing an AhR agonist, is used.

The term "oral composition" has its general meaning in the art and refers to any composition that can be ingested orally.

Typically, the orally ingested composition is selected from the group consisting of a beverage or drink composition, a food composition, a feedstuff composition and a pharmaceutical composition.

The dosage of the AhR agonist or the bacterial probiotic exhibiting AhR activation properties, in particular a bacterial probiotic producing an AhR agonist, is to be appropriately adjusted according criteria such as age, symptoms, body weight, and intended application.

The dosage is selected such as to obtain a therapeutically efficient amount. By therapeutically efficient amount can be defined as the amount necessary for having an impact on one of the five medical conditions defining the metabolic syndrome:

Abdominal (central) obesity (TOF1);
Elevated blood pressure;
Elevating fasting plasma glucose;
High serum triglycerides; and
Low high-density lipoprotein (HDL) levels.

In addition or alternatively, the therapeutically efficient amount can be evaluated by the insulin sensitivity, the glucose tolerance, the weight gain and/or the intestinal inflammation due to HFD. In a preferred embodiment, the therapeutically efficient amount has an impact on several of these conditions.

For example, the amount ingested per day as the bacterial probiotic is typically 0.01 to $100 \times 10^{11}$ cells/body, preferably 0.1 to $10 \times 10^{11}$ cells/body, and more preferably 0.3 to $5 \times 10^{11}$ cells/body. Furthermore, for example, the amount ingested per day as the bacterial probiotic is 0.01 to $100 \times 10^{11}$ cells/60 kg body weight, preferably 0.1 to $10 \times 10^{11}$ cells/60 kg body weight, and more preferably 0.3 to $5 \times 10^{11}$ cells/60 kg body weight.

The content of the bacterial probiotic contained in the orally ingested composition may be determined as appropriate depending on its application form. Typically, as probiotic dry microbial body it is for example 5 to 50 w/w %, preferably 1 to 75 w/w %, and more preferably 0.1 to 100 w/w % and 1 to 100 w/w %.

When an AhR agonist is used for the treatment of the invention, the preferred administration route is enteral or parenteral, preferably by oral, sublingual, subcutaneous, intramuscular, intravenous, transdermal, local or rectal administration, more preferably by oral administration.

Typically, the agent of the invention may be combined with pharmaceutically acceptable excipients, and optionally sustained-release matrices, such as biodegradable polymers, to form therapeutic compositions.

"Pharmaceutically" or "pharmaceutically acceptable" refer to molecular entities and compositions that do not produce an adverse, allergic or other untoward reaction when administered to a mammal, especially a human, as appropriate. A pharmaceutically acceptable carrier or excipient refers to a non-toxic solid, semi-solid or liquid filler, diluent, encapsulating material or formulation auxiliary of any type.

In the pharmaceutical compositions of the present invention for oral, sublingual, subcutaneous, intramuscular, intravenous, transdermal, local or rectal administration, the active principle, alone or in combination with another active principle, can be administered in a unit administration form, as a mixture with conventional pharmaceutical supports, to animals and human beings. Suitable unit administration forms comprise oral-route forms such as tablets, gel capsules, powders, granules and oral suspensions or solutions, sublingual and buccal administration forms, aerosols, implants, subcutaneous, transdermal, topical, intraperitoneal, intramuscular, intravenous, subdermal, transdermal, intrathecal and intranasal administration forms and rectal administration forms.

Preferably, the pharmaceutical compositions contain vehicles which are pharmaceutically acceptable for a formulation capable of being injected. These may be in particular isotonic, sterile, saline solutions (monosodium or disodium phosphate, sodium, potassium, calcium or magnesium chloride and the like or mixtures of such salts), or dry, especially freeze-dried compositions which upon addition, depending on the case, of sterilized water or physiological saline, permit the constitution of injectable solutions.

The pharmaceutical forms suitable for injectable use include sterile aqueous solutions or dispersions; formulations including sesame oil, peanut oil or aqueous propylene glycol; and sterile powders for the extemporaneous preparation of sterile injectable solutions or dispersions. In all cases, the form must be sterile and must be fluid to the extent that easy syringability exists. It must be stable under the conditions of manufacture and storage and must be preserved against the contaminating action of microorganisms, such as bacteria and fungi.

Solutions comprising agents of the invention as free base or pharmacologically acceptable salts can be prepared in water suitably mixed with a surfactant, such as hydroxypropylcellulose. Dispersions can also be prepared in glycerol, liquid polyethylene glycols, and mixtures thereof and in oils.

Under ordinary conditions of storage and use, these preparations contain a preservative to prevent the growth of microorganisms.

The agent of the invention can be formulated into a composition in a neutral or salt form. Pharmaceutically acceptable salts include the acid addition salts (formed with the free amino groups of the protein) and which are formed with inorganic acids such as, for example, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like.

The carrier can also be a solvent or dispersion medium containing, for example, water, ethanol, polyol (for example, glycerol, propylene glycol, and liquid polyethylene glycol, and the like), suitable mixtures thereof, and vegetables oils. The proper fluidity can be maintained, for example, by the use of a coating, such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminium monostearate and gelatin.

Sterile injectable solutions are prepared by incorporating the active agents in the required amount in the appropriate solvent with several of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof.

Upon formulation, solutions will be administered in a manner compatible with the dosage formulation and in such amount as is therapeutically effective. The formulations are easily administered in a variety of dosage forms, such as the type of injectable solutions described above, but drug release capsules and the like can also be employed.

For parenteral administration in an aqueous solution, for example, the solution should be suitably buffered if necessary and the liquid diluent first rendered isotonic with sufficient saline or glucose. These particular aqueous solutions are especially suitable for intravenous, intramuscular, subcutaneous and intraperitoneal administration. In this connection, sterile aqueous media which can be employed will be known to those of skill in the art in light of the present disclosure. Some variation in dosage will necessarily occur depending on the condition of the subject being treated. The person responsible for administration will, in any event, determine the appropriate dose for the individual subject.

In addition to the agents of the invention formulated for parenteral administration, such as intravenous or intramuscular injection, other pharmaceutically acceptable forms include, e.g. tablets or other solids for oral administration; liposomal formulations; time release capsules; and any other form currently used.

Figure 9:
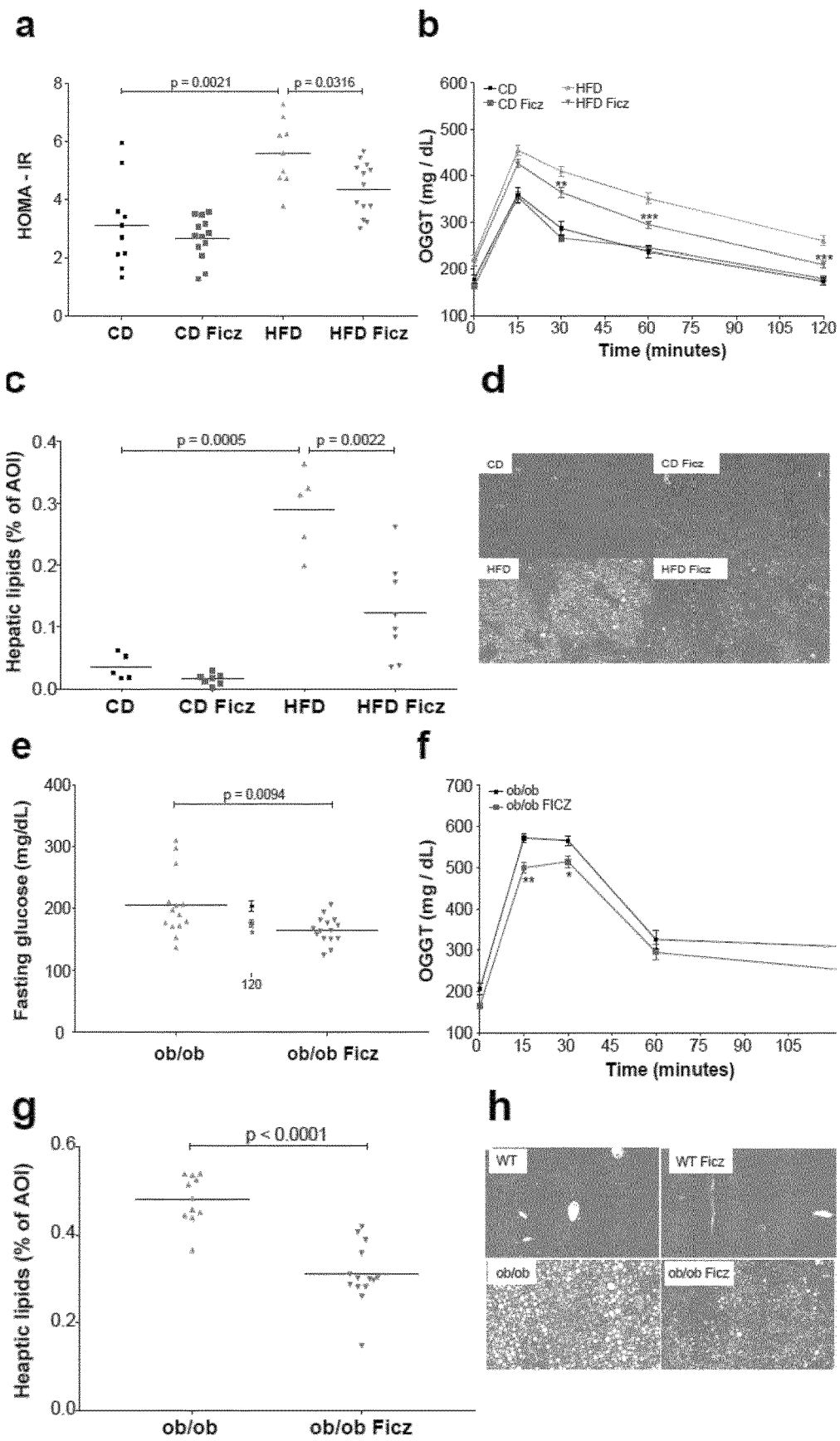
FIG. 9. Treatment with AhR agonist or supplementation with high AhR ligand-producing bacteria alleviates both diet- and genetically-induced metabolic impairments. (a) Fasting homeostatic model assessment-insulin resistance (HOMA-IR) of CD- and HFD-fed mice treated with Ficz or vehicle (DMSO). (b) Blood glucose level before and after oral glucose tolerance challenge of CD- and HFD-fed mice treated with Ficz or vehicle (OGGT, *$p<0.05$ vs HFD, n=12-20/group). (c) Lipid area, calculated as % area of interest (AOI), in liver cross-sections of CD- and HFD-fed mice treated with Ficz or vehicle. (d) Representative pictures of H&E-stained liver sections from CD- and HFD-fed mice treated with Ficz or vehicle. (e) Fasting glucose level of ob/ob mice treated with Ficz or vehicle. (f) Glucose level before and after OGGT of ob/ob mice treated with Ficz or vehicle (*$p<0.05$, n=10-21/group). (g) Lipid area in liver cross-sections of ob/ob mice treated with Ficz or vehicle. (h) Representative pictures of H&E-stained liver sections from ob/ob mice treated with Ficz or vehicle. (i) Quantification of fecal AhR activity of mice fed with CD or HFD supplemented with L. reuteri or vehicle. (j) Fecal concentration of IAA and kynurenine of the indicated mice. Fasting homeostatic model assessment-insulin resistance (HOMA-IR) of CD- and HFD-fed mice supplemented with L. reuteri or vehicle. (k) Blood glucose level before and after OGGT of CD- and HFD-fed mice supplemented with L. reuteri or vehicle (*$p<0.05$, OGGT, n=8/group). (l) Representative pictures of H&E-stained liver sections from CD- and HFD-fed mice supplemented with L. reuteri or vehicle. (m) Lipid area in liver cross-sections of CD- and HFD-fed mice supplemented with L. reuteri or vehicle. For all data, statistical comparison was performed by first testing normality using Kolmogorov-Smirnov test and then ANOVA or Kruskal-Wallis test with Bonferroni or Dunn's post hoc test.

Body weight gain (n=8/group). (b) Blood glucose and (c) insulin after 6 h of fasting. (d) Area under the curve (AUC) of OGGT. Refer to FIG. 9k for the OGGT figure. (e) Blood glucose level before and after insulin tolerance test (ITT; n=8/group). (f) AUC of ITT. Concentration (g) alanine transaminase (ALT), (h) aspartate transaminase (AST) and (i) triglycerides in the serum of indicated mice. Statistical comparison was performed by first testing normality using Kolmogorov-Smirnov test and then unpaired t-test or Mann-Whitney test.

Figure 15:
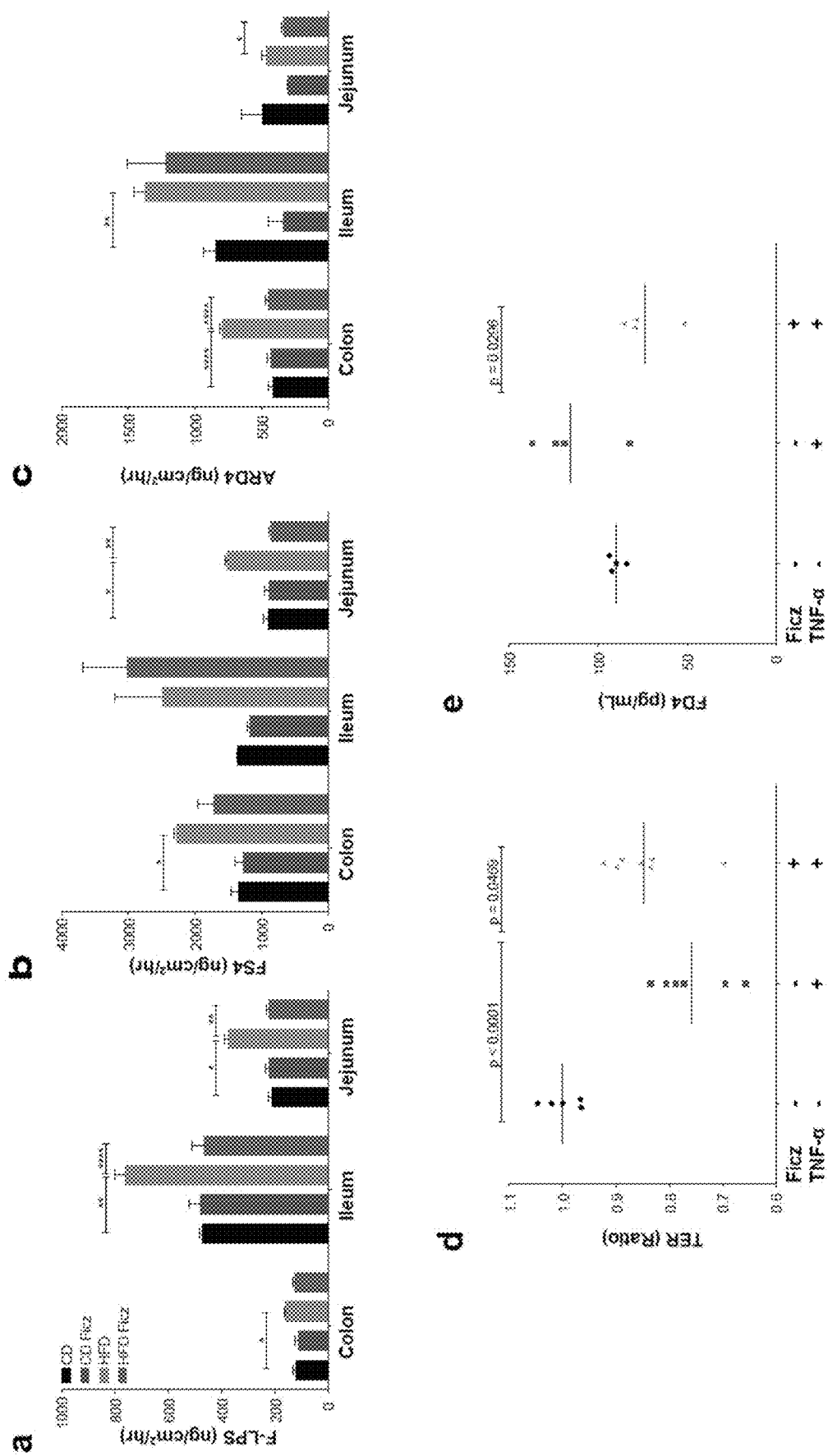
Figure 15:
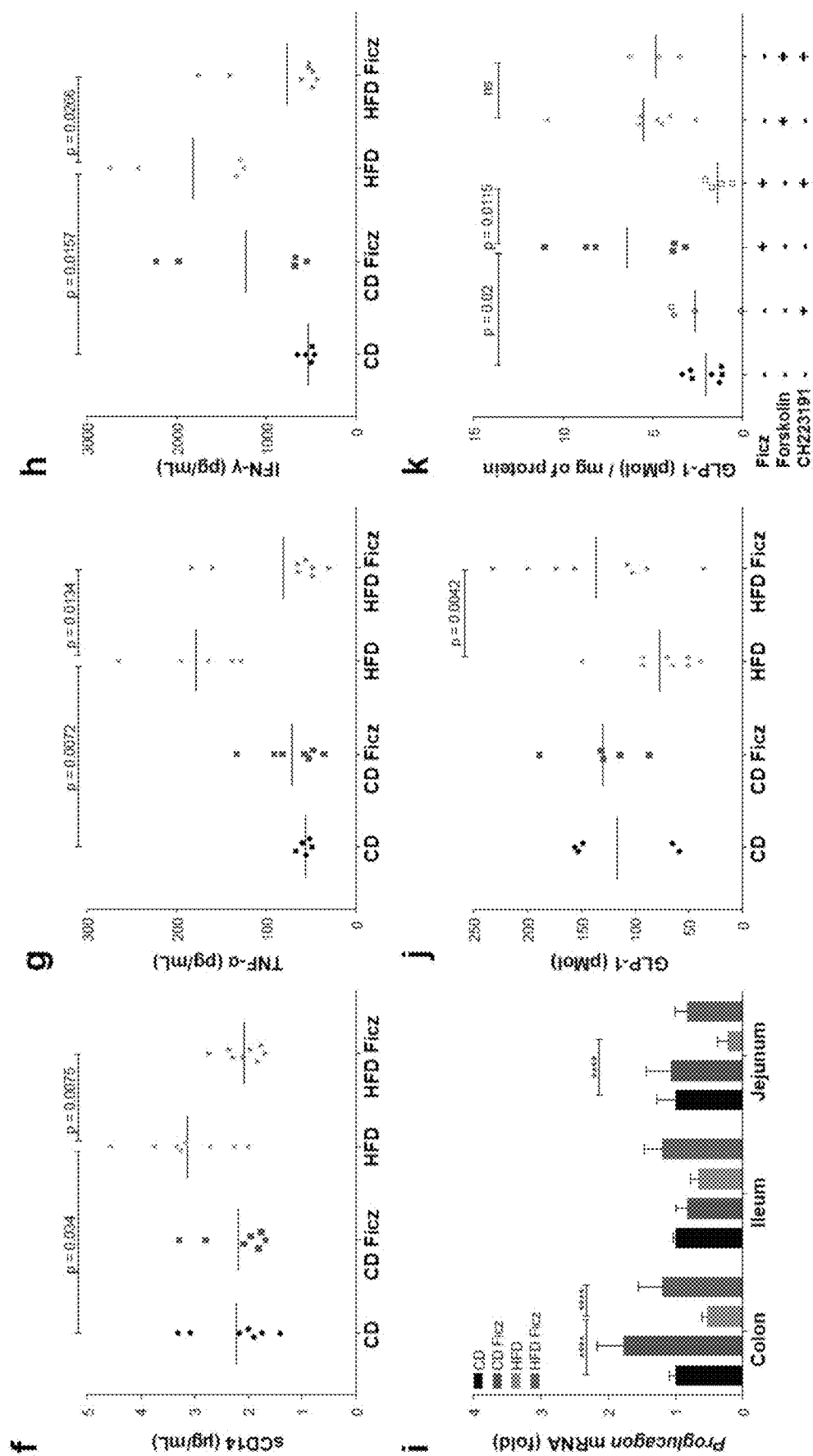

FIG. 15. Treatment with AhR agonist or inoculation with high AhR ligand producing improves HFD-induced intestinal barrier dysfunction and impaired incretin secretion. Translocation of (a) LPS, (b) sulfonic acid (FS4) and (c) dextran (ARD4) across mucosa in different intestinal segments (n=3-5/group). (d-e) Transepithelial resistance (TER) or fluorescein-labeled dextran (FD4) of Caco-2 cells treated with TNF-α or vehicle in the presence of Ficz or vehicle. Data represents one independent experiment. (f) Concentration of soluble CD14 (sCD14) in the serum of indicated mice. (g) TNF-α and (h) IFN-γ production of spleen cells after stimulation with PMA and ionomycin. (i) Expression of proglucagon in different intestinal segments of indicated mice (n=6-8/group). (j) Concentration of total GLP-1 in the serum of indicated mice. (k) Quantification of GLP-1 secretion by GLUTag cells after stimulation with Ficz and forskolin (positive control) in the presence or absence of AhR antagonist (CH223191). Data represents one independent experiment. For all data, statistical comparison was performed by first testing normality using Kolmogorov-Smirnovtest and then ANOVA or Kruskal-Wallis test with Bonferroni or Dunn's post hoc test.

Figure 16:
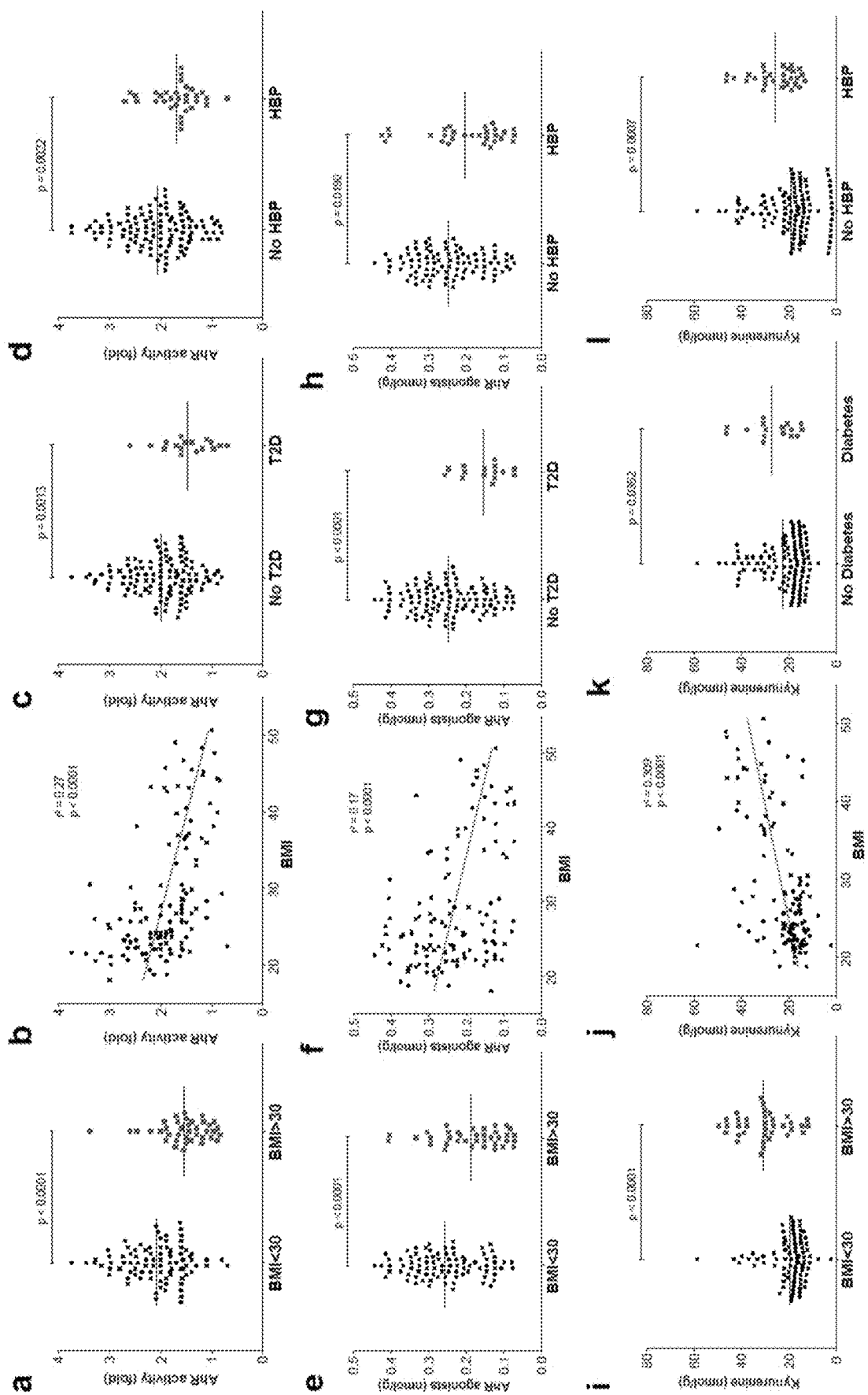

FIG. 16. Microbiota of individuals with metabolic syndrome display reduced AhR activation and lower AhR agonists concentration. (a) Quantification of fecal AhR activity of individuals with low and high body mass index (BMI). (b) Spearman correlation of stool AhR activation and body mass index (BMI). (c-d) Quantification of fecal AhR activity of individuals with type 2 diabetes (T2D) and high blood pressure (HBP) compared to healthy subjects. (e) Total concentration of 4 AhR agonist (IAA, indole, 3-methyl-indole and tryptamine) from feces of individuals with low and high BMI. (f) Spearman correlation of stool AhR agonist concentration and BMI. (g-h) AhR agonist concentration from feces of individuals with T2D and compared to healthy subjects. (i) Kyrunenine concentration from feces of individuals with low and high BMI. (j) Spearman correlation of stool kyrunenine concentration and BMI. (k-l) Kyrunenine concentration from feces of individuals with T2D and compared to healthy subjects. For all data, statistical comparison was performed by first testing normality using Kolmogorov-Smirnov test and then ANOVA or Kruskal-Wallis test with Bonferroni or Dunn's post hoc test.

Figure 17:
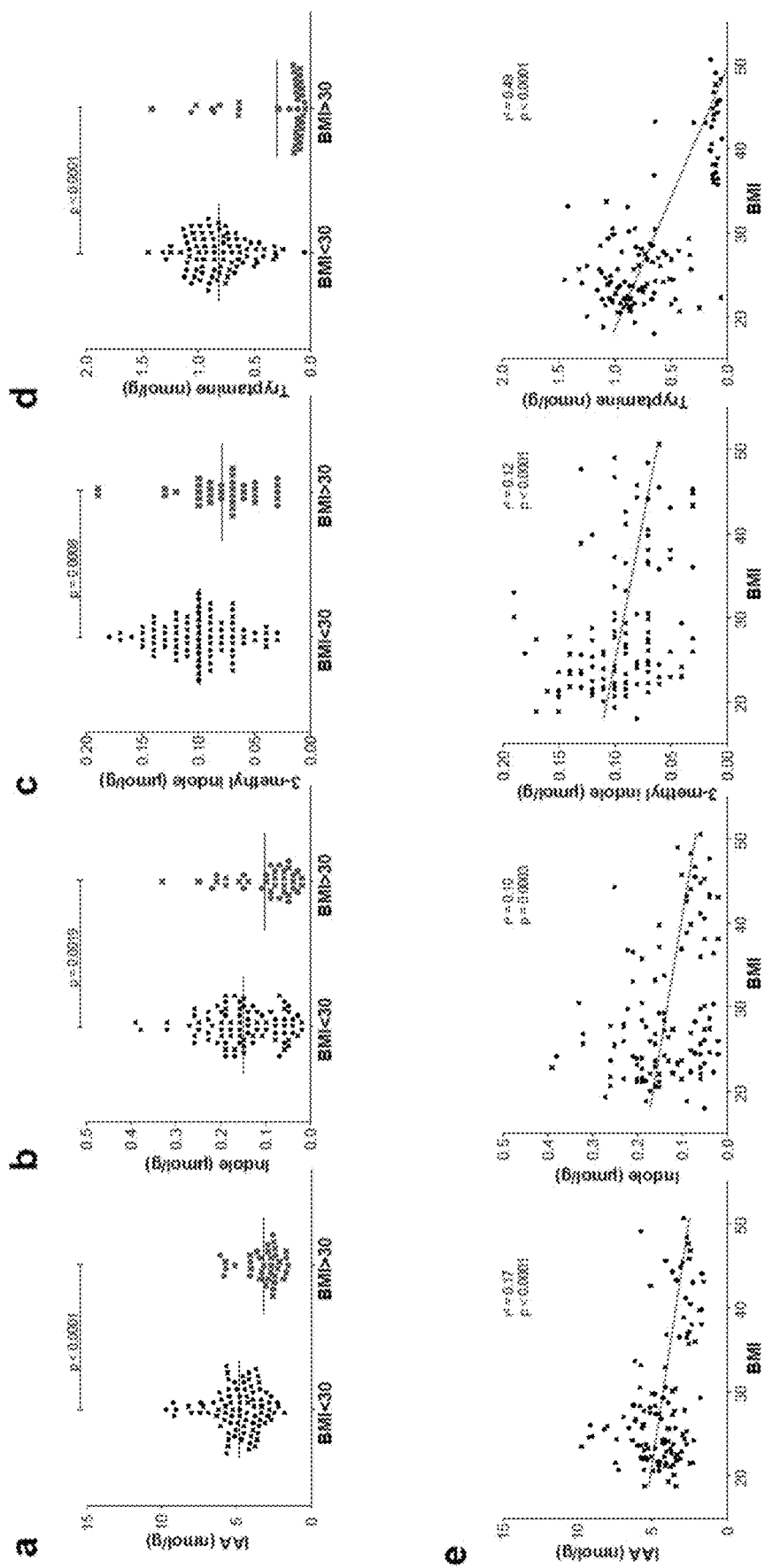

FIG. 17. Microbiota of obese individuals displayed lower levels of microbiota-derived AhR agonists. Concentration of (a) indole acetic acid (IAA), (b) indole, (c) 3-methyl indole and (d) Tryptamine from feces of individuals with low and high BMI. (e) Spearman correlation of stool AhR agonist concentration and BMI. Statistical comparison was performed by first testing normality using Kolmogorov-Smirnov test and then unpaired t-test or Mann-Whitney test.

Figure 18:
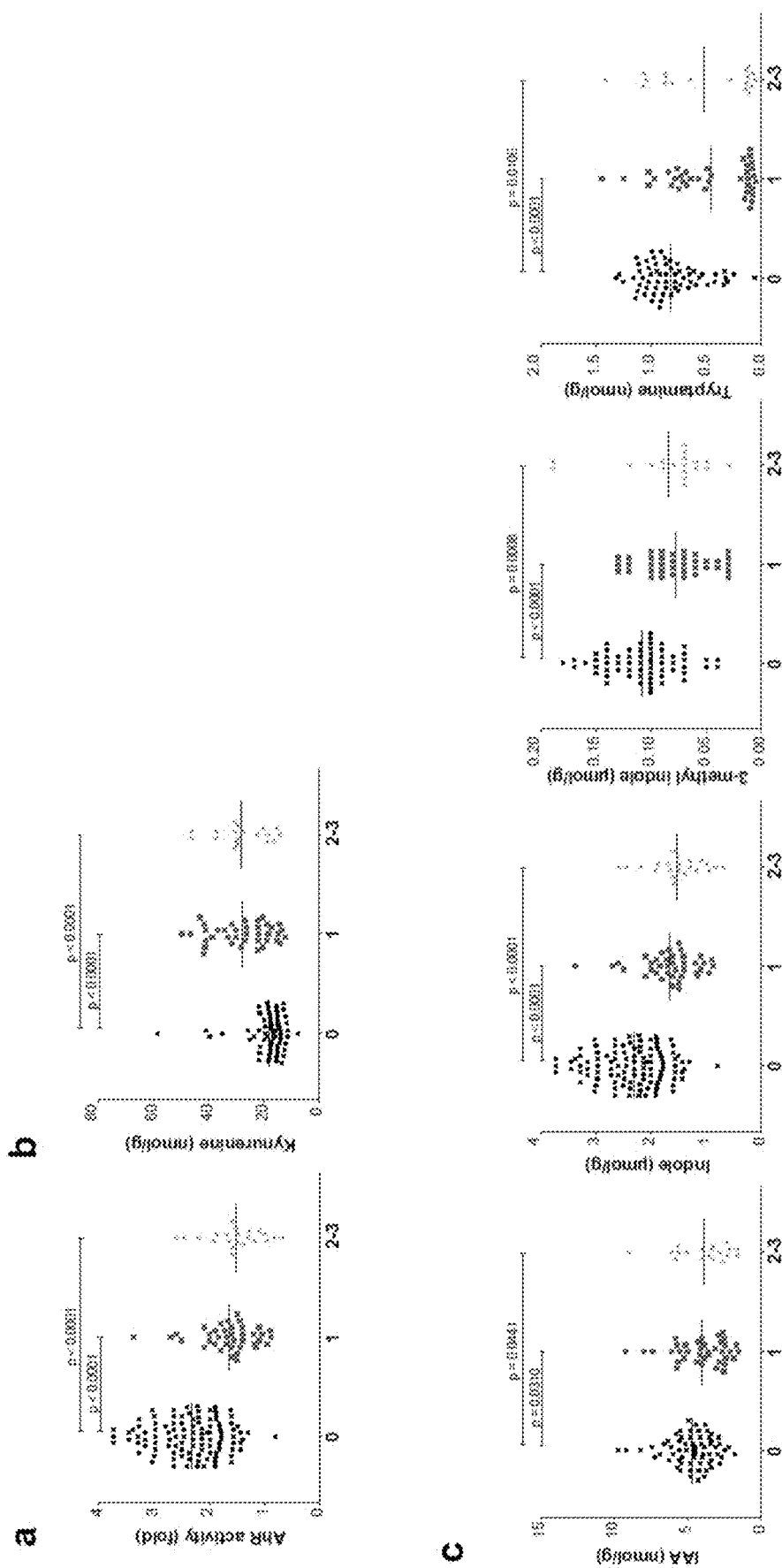

FIG. 18. Microbiota from individuals with metabolic syndrome showed lower AhR activity AhR agonist. Stools from individuals possessing one or more metabolic risk factors showed lower (a) AhR activity, higher (b) kyrunenine and increased level of (c) AhR agonists. Statistical comparison was performed by first testing normality using Kolmogorov-Smirnov test and then unpaired t-test or Mann-Whitney test.

Figure 19:
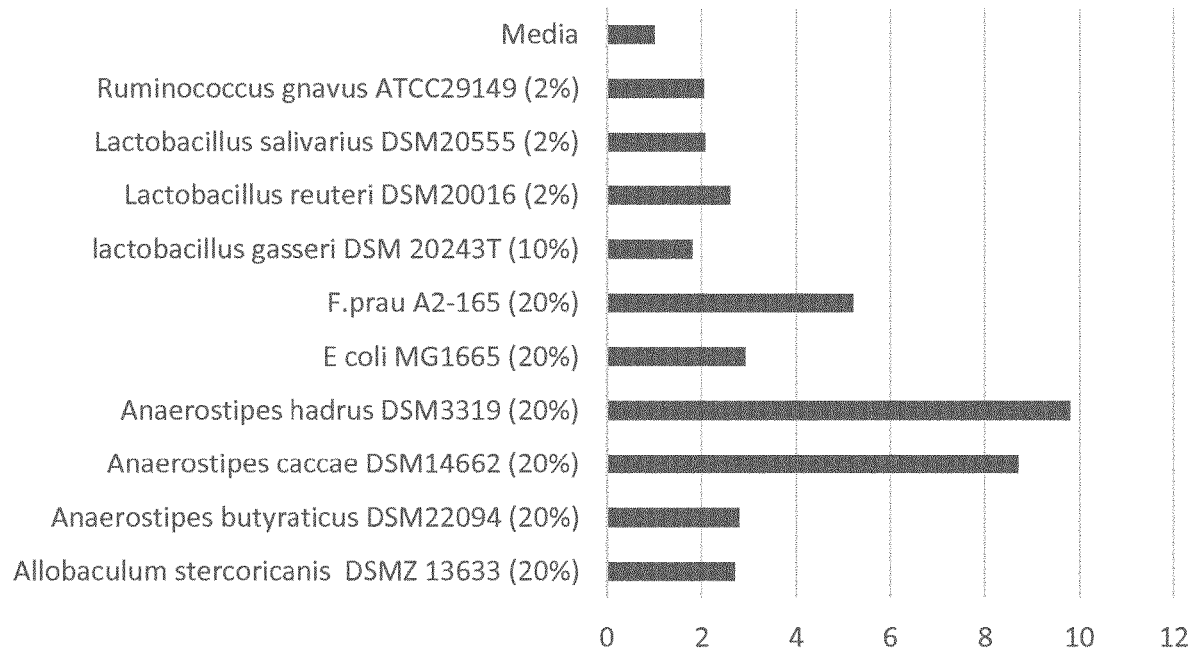
Figure 19:
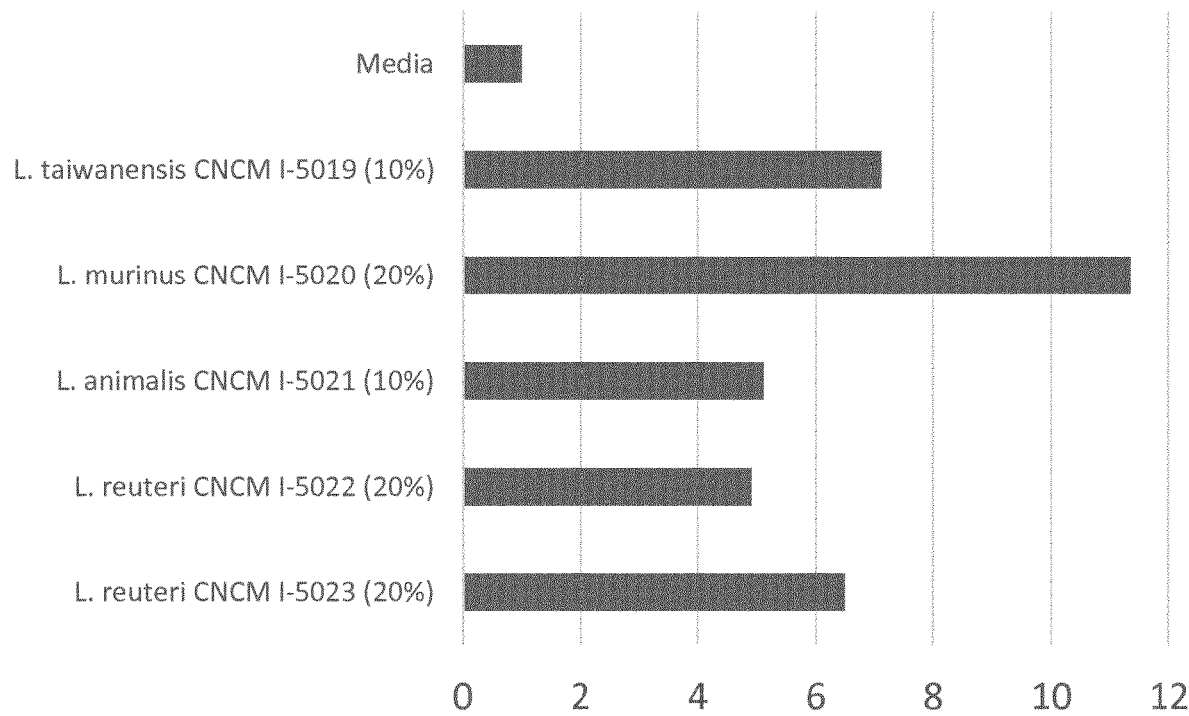

FIG. 19. AhR activity of bacterial strains.

EXAMPLES

Example 1

The inventors explored the role of aryl hydrocarbon receptor (AhR) in modulating high-fat diet (HFD)-induced obesity and insulin resistance. For this, they maintained mice on standard control diet (CD) or high-fat diet (HFD; milk-derived fat) for twelve weeks. They observed a decrease in AhR activity in the feces of mice fed a HFD diet. Moreover, treating the mice with 6-Fomylindolo-(3,2-b) carbazole (FICZ), a potent AhR agonist, reduced the weight gain and markedly improved glucose tolerance in HFD-fed mice. This study indicates a critical role of AhR activation in the regulation of high-fat diet induced obesity, insulin resistance and dysregulated immune response.

Results

Analysis of AhR Activity in HFD-Fed Mice.

After 12 weeks of CD or HFD, AhR activity in the feces was analyzed using a luciferase reporter-based assay (Lamas et al, 2016). Ileal and colonic expressions of AhR-regulated genes were similarly evaluated. As shown in the FIG. 1, the AhR fecal activity of HFD-DMSO mice was significantly reduced compared to CD-DMSO mice. This was associated with a lower expression of AhR-related genes, such as the cytokine Il22 and the antimicrobial Reg3g and Reg3b. Intraperitoneal injection of FICZ, an AhR agonist, rescued Il22 and Reg3g expression in colon and ileum of mice fed a HFD diet without changing the fecal AhR activity.

Figure 2:
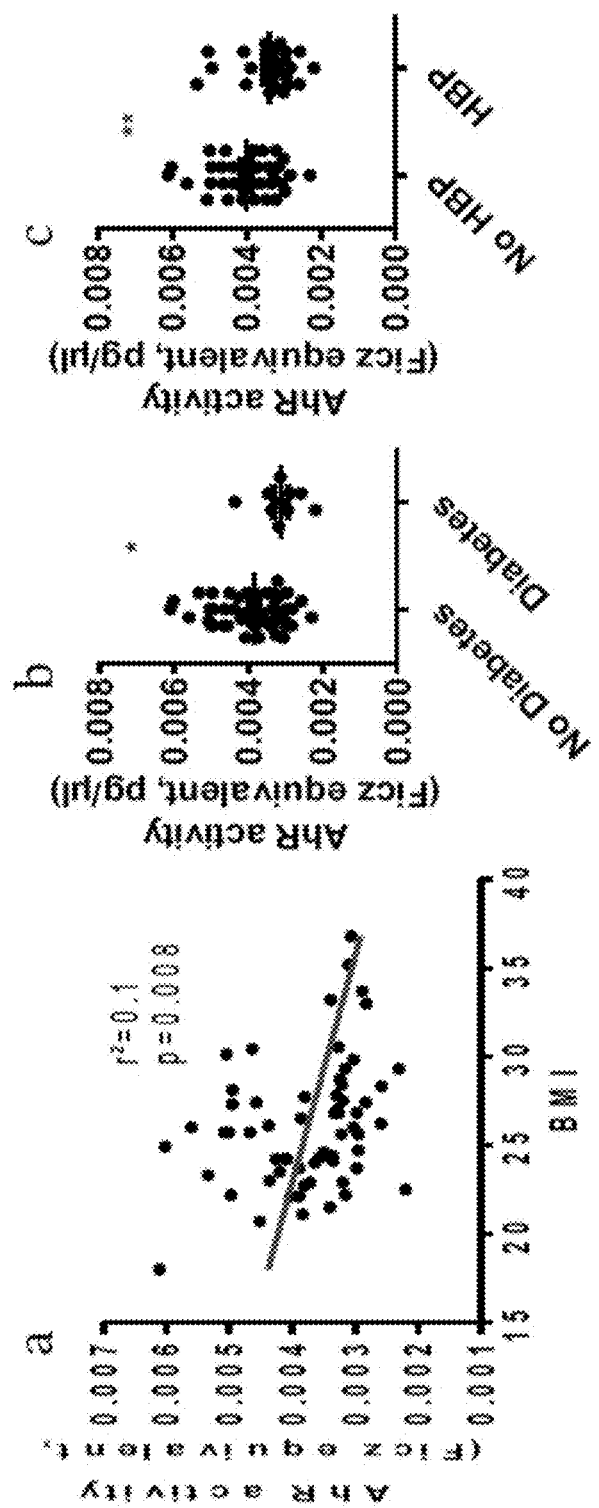
FIG. 2. Defective AhR agonist activity of the gut microbiota in metabolic syndrome in human. In human, AhR agonist activity of the gut microbiota is negatively correlated with body mass index (BMI) (A), and is lower in patients with diabetes (B) or high blood pressure (HBP) (C). In all panels, *$P<0.05$,  or $^{\dagger\dagger}P<0.001$, and * or $^{\dagger\dagger\dagger}P<0.0001$, two-tailed Student's t-test in panels. Spearman correlation used in panel A.

Reduced AhR Activity in the Microbiota of Human Patients with Metabolic Syndrome To assess whether the phenomenon observed in mice have a clinical relevance in humans, the inventors analyzed fecal samples from a cohort of patients in consulting in cardiology for their ability to activate AhR. As shown in the FIG. 2, they observed a correlation between AhR activity and (i) the body mass index (BMI), (ii) blood pressure and (iii) diabetes status. The results suggest that the microbiota of obese patients and/or patients with metabolic syndrome have an impaired ability to produce AhR ligands which could be involved in the pathogenesis of metabolic syndrome.

Effect of AhR Activation on Weight Gain and Food Intake.

Figure 3:
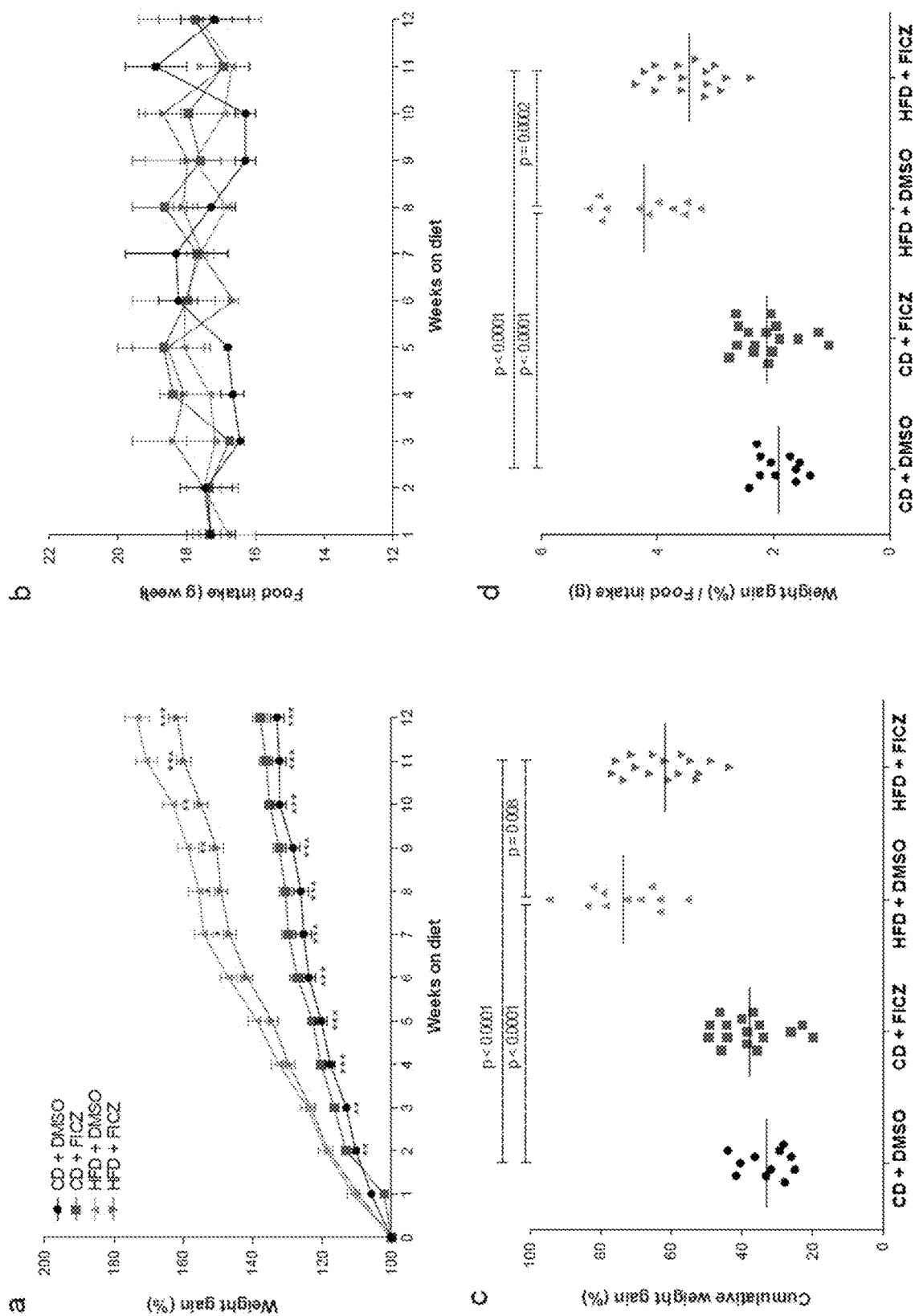
FIG. 3. AhR agonist reduced HFD-induced weight gain independent of food intake. (a) Weight gain in CD- and HFD-fed mice treated with FICZ or vehicle (DMSO). (b) Weekly food intake in CD- and HFD-fed mice. In a-b, data are shown as mean±SEM (n=11-16/group) and statistical comparison was performed using two-way analysis of variance followed by Bonferroni post-hoc test. Statistical significance: *$P<0.05$, $P<0.01$, *$P<0.001$ vs HFD-DMSO. (c) Body weight gain of mice that were fed with CD- or HFD for 12 weeks with or without FICZ treatment. (d) Body weight gain normalized to food intake of mice that were fed with CD- or HFD for 12 weeks with or without FICZ treatment. In c-d, statistical comparison was performed by first testing normality using Kolmogorov-Smirnov test and then multiple comparison test using one-way analysis of variance (ANOVA) followed by Bonferroni post-hoc test or Kruskal-Wallis test followed by Dunn's post-hoc test.

Food consumption and weight gain were recorded weekly. All HFD-fed mice exhibit higher weight gain compared to mice fed a CD diet. As shown in FIG. 3, HFD-fed mice treated with FICZ showed significantly lower weight gain compared to untreated HFD-fed mice. During the course of the experiment, no significant difference in food consumption was detected between FICZ treated and untreated HFD-mice, suggesting that lower weight gain in HFD-FICZ group was independent of reduced food intake by mice.

Effect of AhR Activation on HFD-Induced Glucose Tolerance and Insulin Sensitivity.

Figure 4:
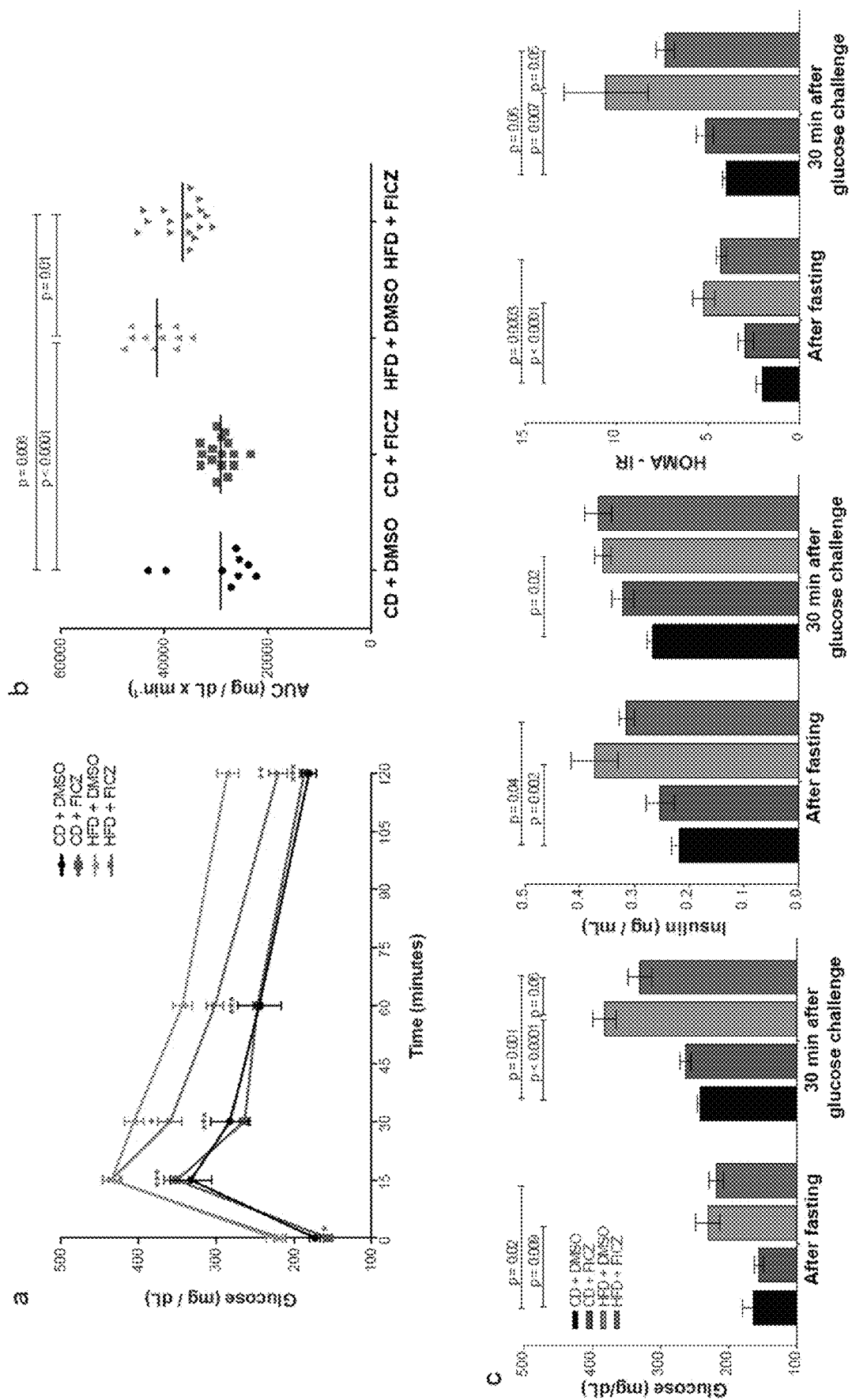
FIG. 4. AhR agonist improved HFD-induced glucose tolerance. (a) Oral glucose tolerance test on mice fed with either CD or HFD with or without FICZ treatment. Data are shown as mean±SEM (n=11-16/group) and statistical comparison was performed using two-way analysis of variance followed by Bonferroni post-hoc test. Statistical significance: *$P<0.05$, $P<0.01$, *$P<0.001$ vs HFD-DMSO (b) Area under the curve (AUC) calculation (calculated from figure a) during oral glucose tolerance test. (c) Glucose, insulin and homeostatic model assessment (HOMA) calculation after 6 h of fasting and 30 min after oral glucose challenge. In b-c, data shown are expressed as mean±SEM (n=11-16/group) and statistical comparison was performed by first testing normality using Kolmogorov-Smirnov test and then multiple comparison test using one-way analysis of variance (ANOVA) followed by Bonferroni post-hoc test or Kruskal-Wallis test followed by Dunn's post-hoc test.

After 11-weeks of CD or HFD, glucose homeostasis was evaluated using the oral glucose tolerance test (OGGT) method. In brief, after 6 hours of fasting, mice were challenged orally with glucose (2 g/kg of weight), and glucose and insulin levels were measured regularly within the two-hour period after challenge. As shown in FIG. 4, HFD-fed mice, regardless of treatment, showed higher fasting glucose and insulin levels compared to CD-fed mice. However, HFD-FICZ mice showed better glucose tolerance and insulin sensitivity after glucose challenge compared to non-treated HFD-fed mice. Overall, the results showed that activating AhR axis, using FICZ, rectified HFD-induced glucose tolerance.

Effect of AhR Activation on HFD-Induced Systemic Immune Response.

Figure 5:
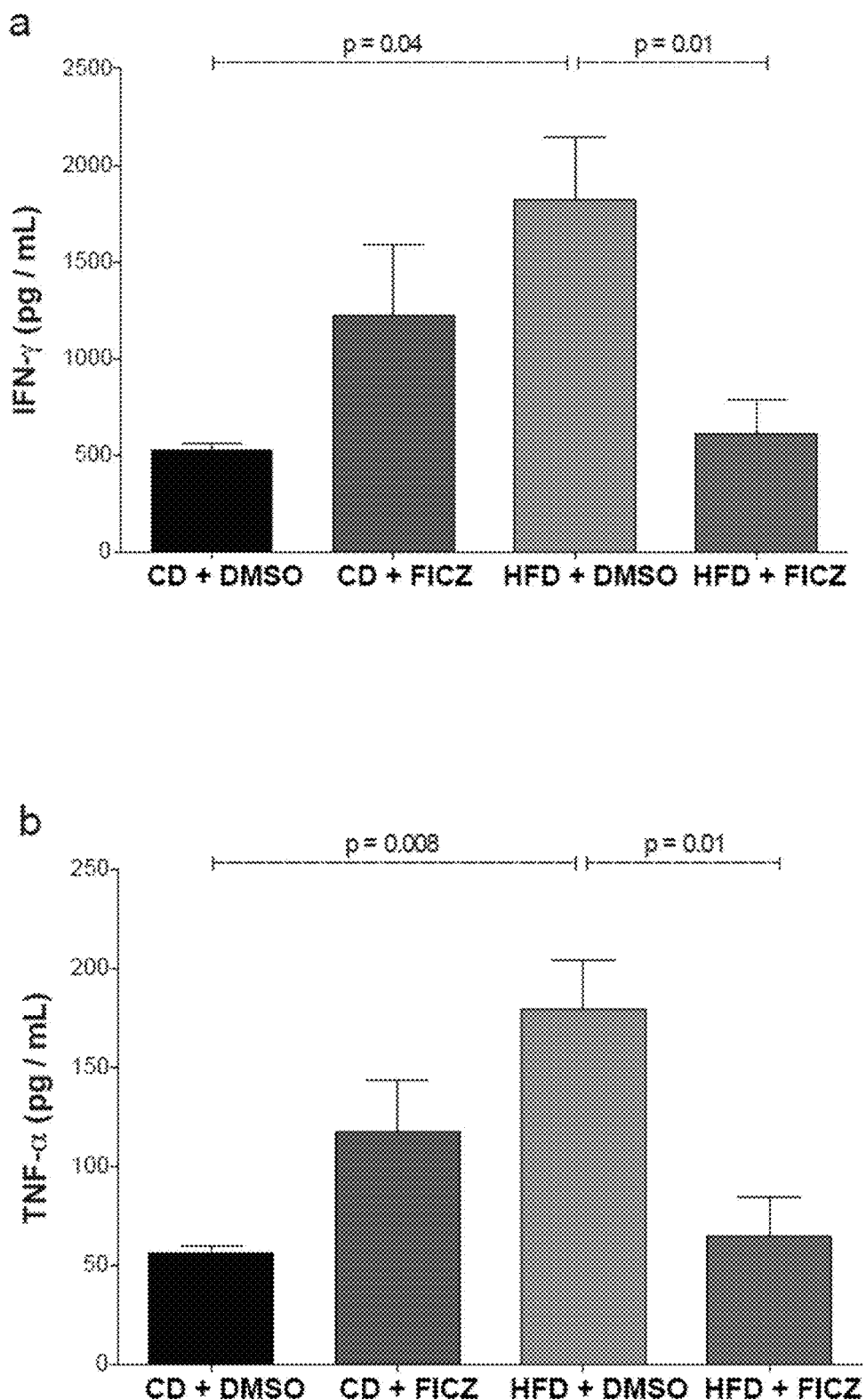
FIG. 5. AhR agonist prevented HFD-induced dysregulated immune response in spleen. Quantification of (a) IFN-γ (b) TNF-α (c) IL-17α and (d) IL17f cytokine production by anti-CD3/anti-CD28-stimulated splenic cells from CD- and HFD-fed mice treated with or without FICZ. Data shown are expressed as mean±SEM (5-8/group). Statistical comparison was performed by first testing normality using Kolmogorov-Smirnov test and then multiple comparison test using one-way analysis of variance (ANOVA) followed by Bonferroni post-hoc test or Kruskal-Wallis test followed by Dunn's post-hoc test.
Figure 5:
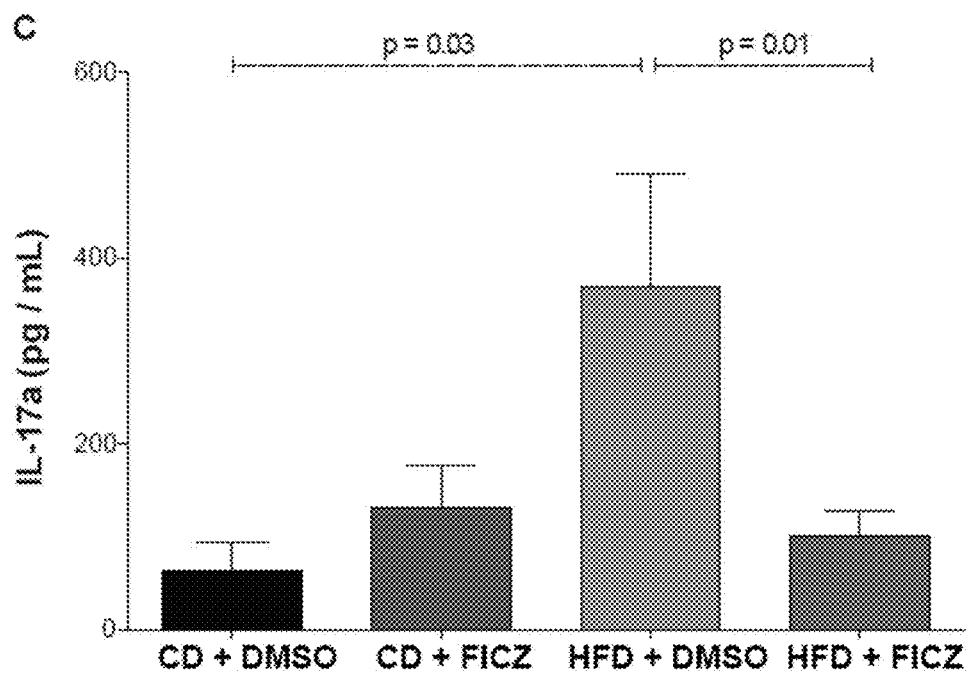
Figure 5:
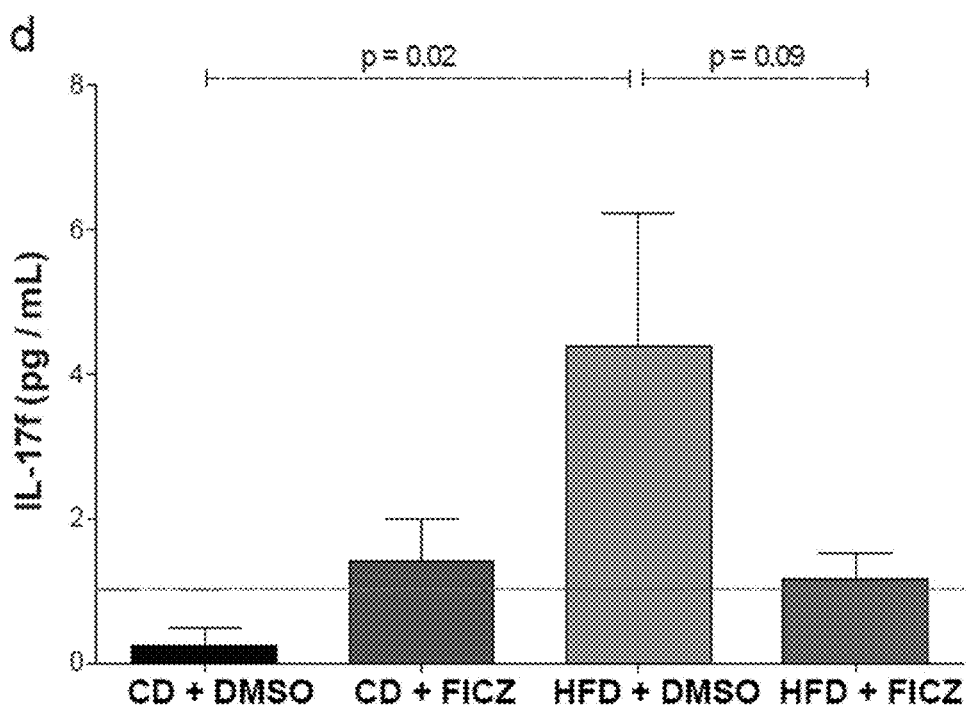

Cytokine production of splenic cells from CD- or HFD-fed mice was measured after in vitro anti-CD3 and anti-CD28 stimulation using cytokine multiplex assay. As shown in FIG. 5, HFD-DMSO mice showed higher IFN-γ, TNF-α, IL-17a and IL17f production compared to CD-DMSO mice. FICZ treatment in HFD-fed mice rescued the production of this cytokines reaching the level of CD-DMSO mice showing that, FICZ reversed the HFD-induced dysregulated systemic immune response.

Effect of AhR Activation on HFD-Induced Mucosal Immune Response.

Figure 6:
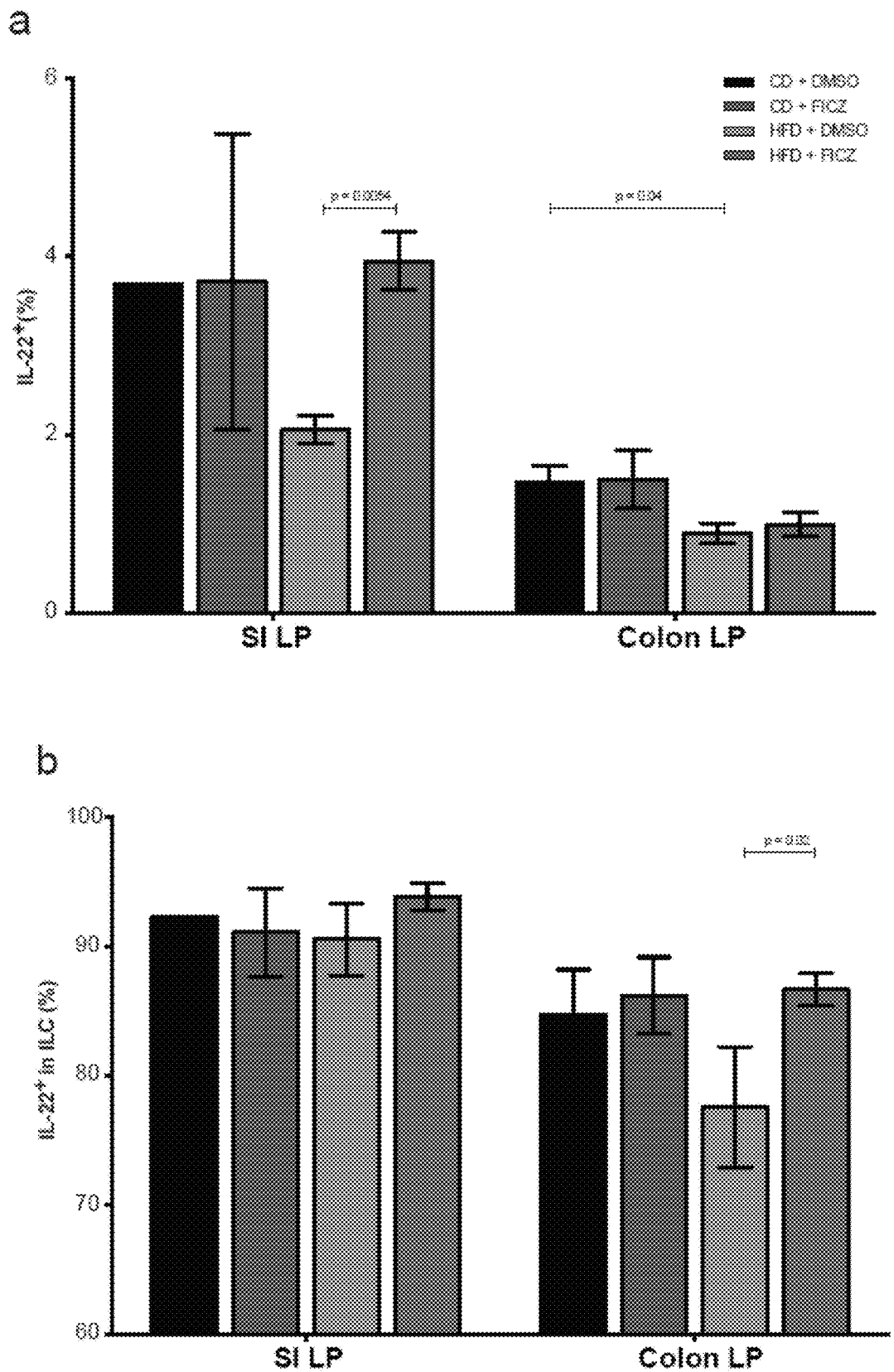
FIG. 6. AhR agonist prevented HFD-induced dysregulated mucosal immune response. (a) Quantification of IL-22+ cells isolated from small intestine (SI) and colon lamina propria (LP). Cells were gated on total live cells. (b) Quantification of IL-22+ cells within ILC population. Cells were gated on no T-cells, B-cells, dendritic cells and monocytes population. (c) Quantification of lamina propria (LP) and intraepithelial lymphocytes (IEL) IFN-γ+ cells isolated from small intestine (SI) and colon. Cells were gated on total live cells. Data shown are expressed as mean±SEM (2-6/group). Statistical comparison was performed by first testing normality using Kolmogorov-Smirnov test and then multiple comparison test using one-way analysis of variance (ANOVA) followed by Bonferroni post-hoc test or Kruskal-Wallis test followed by Dunn's post-hoc test.
Figure 6:
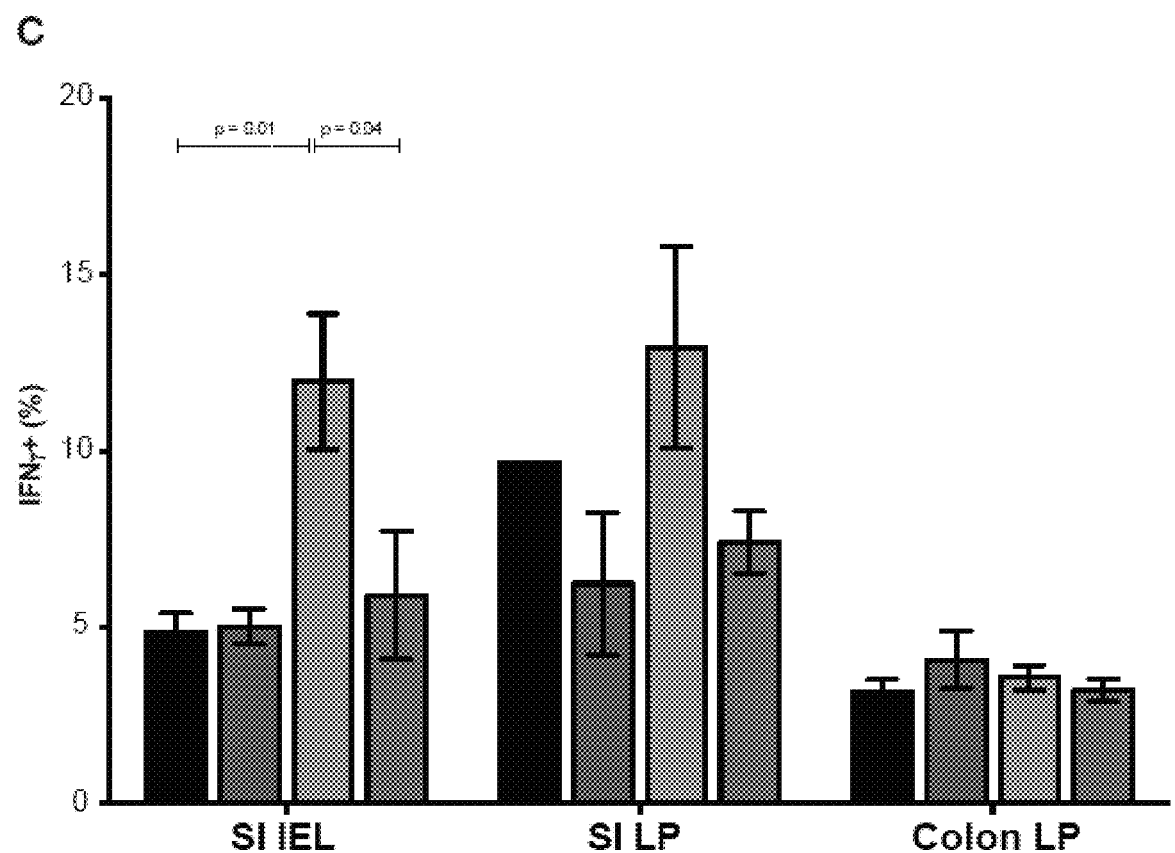

Lamina propria (LP) and intestinal epithelial cells from small intestine (SI) and colon were isolated and stimulated with phorbol 12-myristate 13-acetate (PMA) and ionomycin for 4 h. IL-22+ and IFN-γ+ cells were quantified by flow cytometry technique. As shown in FIG. 6, SI and colon cells of HFD-DMSO mice showed lower total IL-22 production compared to CD-DMSO mice. The percentage of innate lymphoid cells (ILC) producing IL-22 was also reduced in colon LP of HFD-DMSO mice. HFD was associated with increased production of IFN-γ by SI LP cells and intestinal epithelial lymphocytes (IEL). FICZ treatment reversed the HFD-induced SI LP and colonic innate lymphoid cells IL-22 deficiency. Furthermore, AhR activation by FICZ reduced the HFD-induced IFN-γ production in the small intestine.

Conclusion

This work shows that a HFD diet induces an alteration in the ability of the intestinal microbiota to produce AhR agonists, leading to a defect in IL-22 pathway. Activating the AhR machinery is effective in correcting these defects and confers a protective effect on weight, glycemic control and intestinal inflammation induced by HFD diet.

The present results have a relevant translational impact for humans, as impaired ability to produce AhR ligands is observed in obese patients and/or patients suffering from metabolic syndrome. Two studies have suggested that AhR activation is deleterious in metabolic syndrome (Kerley-Hamilton et al Environ Health Perspect 2012; Xu et al Int J Obes (Lond), 2015). However these two studies, were conducted with AhR knockout mice (or mice with a diminished sensitivity in a comprehensive manner with respect to AhR). On the contrary, the inventors' work suggests that a defect of AhR ligands in the intestine (without pre-judging the systemic effect) is pathogenic for the development of metabolic syndrome.

Materials and Methods

Mice and Treatments.

C57BL/6J mice (Janvier) were maintained under specific pathogen free (SPF) conditions. All mice were males and 4 weeks of age at the start of the experiments. Mice were weight matched at the start of the experiments. Mice were fed with irradiated control diet (CD; Envigo MD 120508) or high-fat diet (HFD; Envigo MD 972222) containing 18% Milk-fat for 12 weeks. Fomylindolo-(3,2-b) carbazole (FICZ) and vehicle (DMSO) were injected intraperitoneally 3 days after switching the diet to CD or HFD and then 1× per week until the end of the experiment. Tissue samples were harvested at the end of the experiment. Weekly food consumption was measured cage-wise.

Luciferase Assay for AhR Activity Measurement.

AhR activity in the feces was measured as previously described (Lamas et al, 2016). Briefly, frozen stool samples from mice, healthy subjects and patients suffering from obesity or metabolic syndrome were diluted in PBS, centrifuged, filtered and then used to treat H1L1.1c2 cell line, containing a stably integrated dioxin-response element (DRE)-driven firefly luciferase reporter plasmid pGud-Luc1.1. 24 h after incubation, cells were lysed and luciferase activity was measured using a luminometer. The results were normalized based on the negative luciferase activity of the control.

Gene Expression Analysis Using Quantitative Reverse-Transcription PCR.

RNA isolation, cDNA preparation and qPCR analysis were conducted as previously described (Lamas et al, 2016). The oligonucleotides used were as follows: Gapdh (sense) 5'-AACTTTGGCATTGTGGAAGG-3' (SEQ ID No 1) and (antisense) 5'-ACACATTGGGGGTAGGAACA-3' (SEQ ID No 2); Il22 (sense) 5'-CATGCAGGAGGTGGTACCTT-3' (SEQ ID No 3) and (antisense) 5'-CAGACGCAAGCAT-TTCTCAG-3' (SEQ ID No 4); Reg3g (sense) 5'-TTCCTGTCCTCCATGATCAAAA-3' (SEQ ID No 5) and (antisense) 5'-CATCCACCTCTGTTGGGTTCA-3' (SEQ ID No 6); and Reg3b (sense) 5'-ATGCTGCTCTCCTGCCTGATG-3' (SEQ ID No 7) and (antisense) 5'-CTAATGCGTGCGGAGGGTATATTC-3' (SEQ ID No 8). Gene expression was analyzed using 2-ΔΔCt quantification method, with mouse Gapdh as an endogenous control and the CD group as a calibrator.

Glucose Tolerance Test and Insulin Measurement.

Oral glucose tolerance tests were performed after 11 weeks of diet. Food and bedding was removed on the onset of the daylight cycle and mice were treated after a 6 h fasting period with an oral gavage glucose load (2 g per kg body weight). Blood glucose was measured before fasting, before oral glucose load and 15, 30, 60, 120 min after oral glucose challenge. Blood insulin was measured before oral glucose load and 30 min after oral glucose load. Blood glucose and insulin were determined with a glucose meter (Accu Chek Aviva, Roche) and Ultrasensitive ELISA kit (Alpco), respectively, on blood samples collected from the tip of the tail vein.

Cytokine Quantification.

Single cell suspensions from spleens were prepared using mechanical disruption method and then stimulated for 48 h with phorbol 12-myristate 13-acetate (PMA, 50 ng/mL; Sigma-Aldrich) and ionomycin (1 laM; Sigma-ALdrich). Cytokines in the culture supernatants were quantified using commercial cytokine ELISA kits (Ebioscience or R&D) or bead-based immunoassay (Biolegend Legendplex).

Lamina Propria Cell Isolation and Flow Cytometry.

Single cell suspensions from the colon and small intestine lamina propria were isolated and stained as previously described (Lamas et al, 2016). The following antibodies were used for surface staining of: CD3 (145-2C11, eBioscience); CD4 (L3T4, BD); CD11b (M1/70, eBioscience); CD11c (N418, eBioscience); F4/80 (BM8, eBioscience). Intracellular cytokine staining was performed using IL-22 (IL-22JOP, eBioscience) and IFN-γ (XMG1.2, eBioscience) antibodies. The cells were analyzed using a LSR Fortessa cell analyzer (BD). Lymphocytes were gated using forward scatter (FSC) and side scatter (SSC).

Example 2

Here, the inventors show that in both diet- and genetically-induced animal models of metabolic syndrome, the gut microbiota exhibits reduced production of AhR ligands. Supplementation with AhR agonist or *Lactobacillus* strain with high natural tryptophan-metabolic activity was sufficient to decrease the hallmark features of metabolic syndrome, including insulin resistance and liver steatosis. The mechanisms involved include correction of the altered intestinal barrier function, a condition often observed in metabolic syndrome7, and rectification of the intestinal incretin hormone GLP-1 secretion. Impaired AhR activity of the microbiota, consistent with lower concentrations of AhR ligands, was similarly observed in humans with metabolic syndrome.

Results

Figure 1:
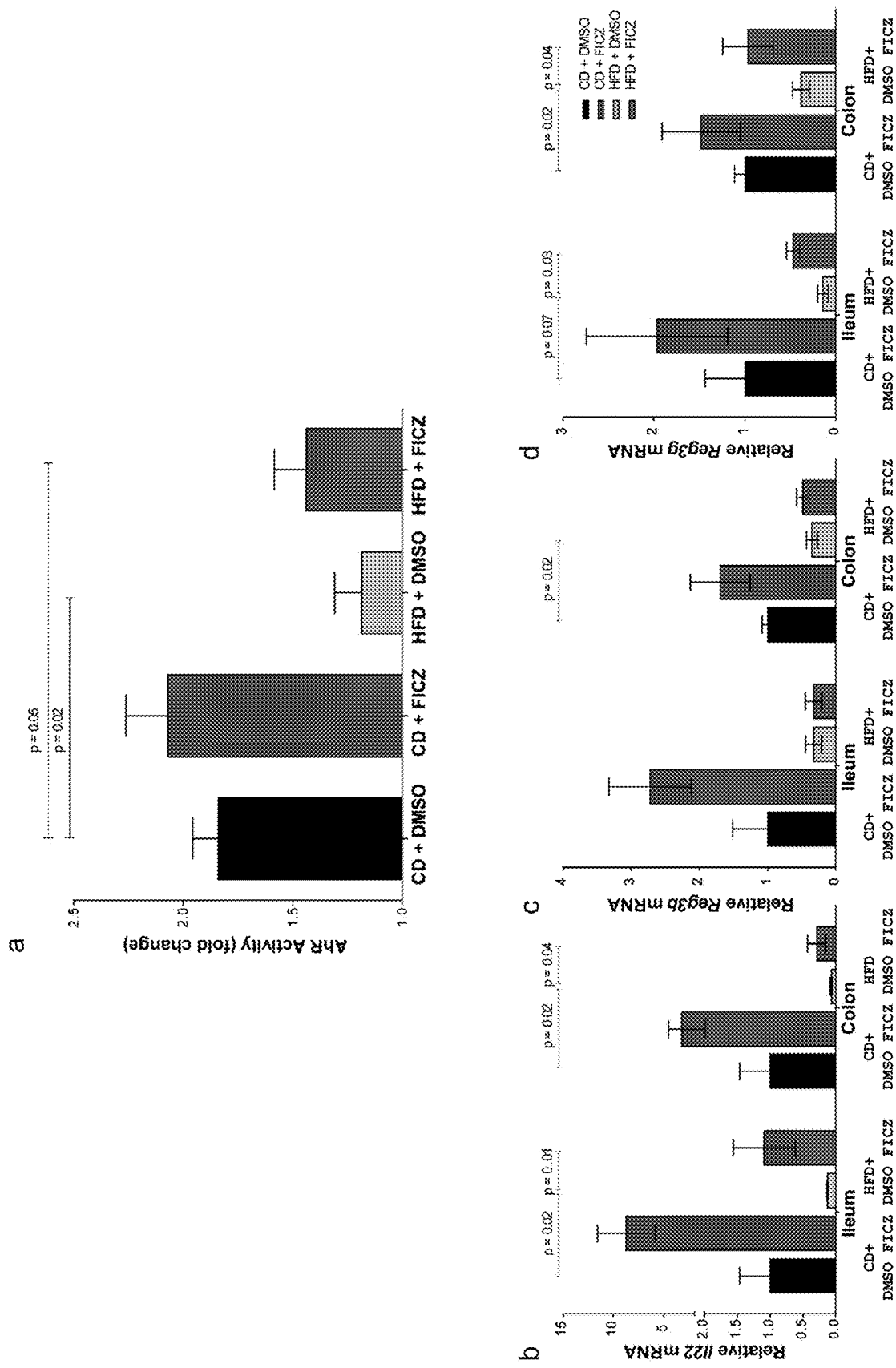
FIG. 1. AhR agonist reversed HFD-induced IL-22 deficiency. (a) Fecal AhR activity from indicated mice fed with either CD or HFD diet. Data are shown as mean±SEM (n=5-10/group). Quantification of (b) Il22 (c) Reg3b and (d) Reg3g mRNA transcripts by RT-qPCR method in ileum and colon of CD- and HFD-fed mice treated with FICZ or vehicle (DMSO). In b-d, data were quantified using $\Delta\Delta Ct$ with Gapdh as internal control and CD-DMSO group as a calibrator, and expressed as mean±SEM (5-8/group). In a-d, statistical comparison was performed by first testing normality using Kolmogorov-Smirnov test and then multiple comparison test using one-way analysis of variance (ANOVA) followed by Bonferroni post-hoc test or Kruskal-Wallis test followed by Dunn's post-hoc test.
Figure 7:
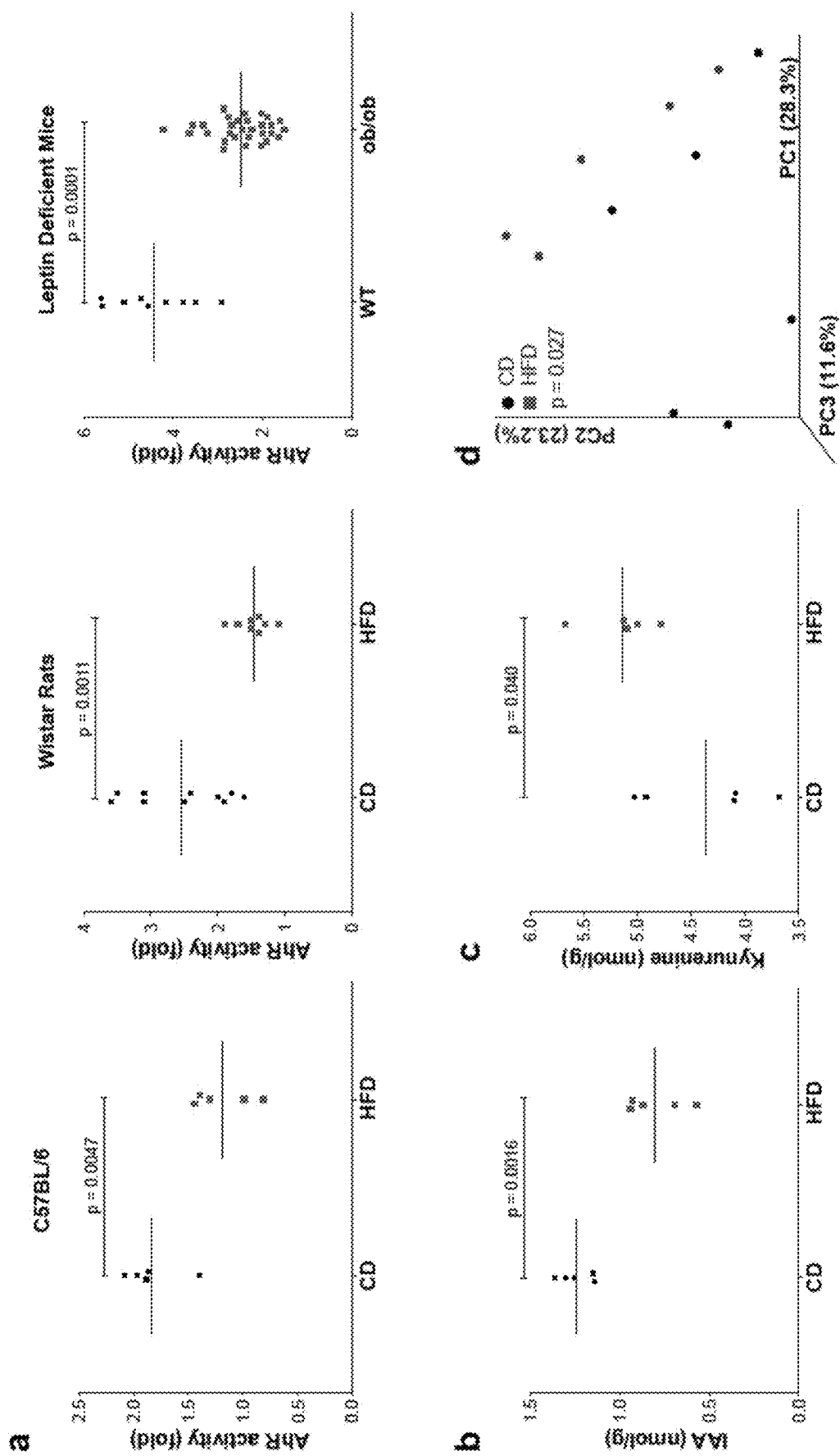
FIG. 7. Diet- and genetically-induced metabolic syndrome is associated with altered microbiota composition and impaired microbiota-driven AhR activation. (a) Quantification of fecal AhR activity of mice (left) and rats (middle) fed with CD or HFD for 12 weeks, and ob/ob and wild-type (WT) mice fed with CD at 6 weeks of age. (b) Fecal concentration of indole acetic acid (IAA) and kynurenine of the indicated mice. (c) PCoA plot of fecal microbiota of mice fed with CD or HFD after 12 weeks. (d) Bar graph of bacterial abundance in family level of CD- or HFD-fed mice. For figure a-b, statistical comparison was performed by first testing normality using Kolmogorov-Smirnov test and then ANOVA or Kruskal-Wallis test with Bonferroni or Dunn's post hoc test.
Figure 8:
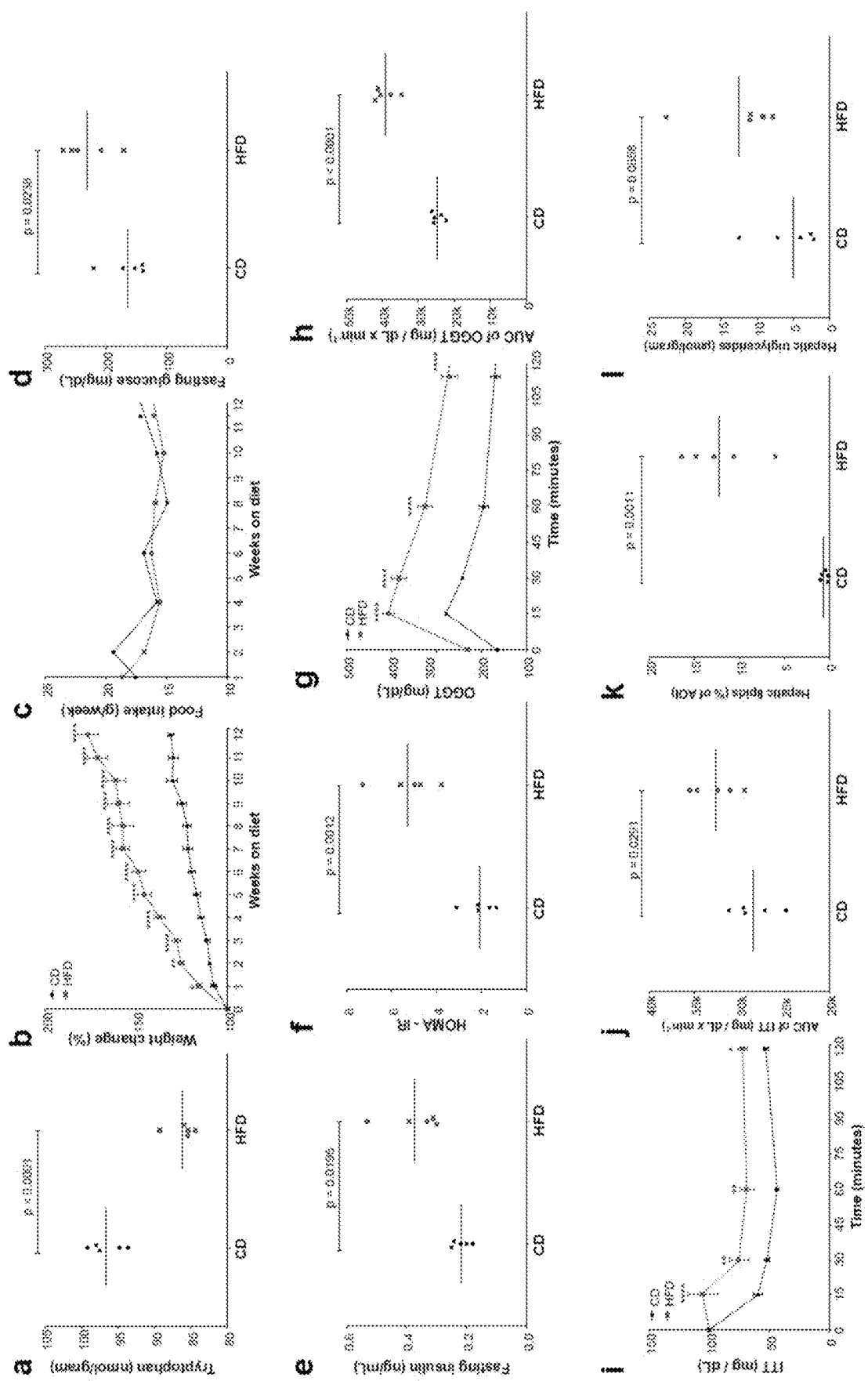
FIG. 8. HFD-fed mice showed defective tryptophan metabolism by microbiota and metabolic host dysfunctions. (a) Concentration of tryptophan in the colon mucosa of mice fed with CD or HFD. (b) Body weight gain and (c) weekly food intake of mice (*$p<0.05$, n=5/group). (d) Blood glucose, (e) insulin, (f) homeostatic model assessment-insulin resistance (HOMA-IR) after 6 h of fasting. (g) Blood glucose level before and after oral glucose tolerance challenge (OGGT; *$p<0.05$, n=5/group). (h) Area under the curve (AUC) of OGGT. (i) Blood glucose level before and after insulin tolerance test (ITT; n=5/group). (j) Area under the curve (AUC) of OGGT. (k) Lipid area, calculated as % area of interest (AOI), in H&E stained liver cross-sections. (l) Liver triglycerides after 6 h of food deprivation. Statistical comparison was performed by first testing normality using Kolmogorov-Smirnov test and then unpaired t-test or Mann-Whitney test.

Products of tryptophan metabolisms are among the key microbiota-derived metabolites involved in microbiota-host crosstalk. Indeed, the inventors showed that the inefficiency of gut microbiota to metabolize tryptophan into AhR ligands is involved in the pathogenesis of inflammatory bowel disease, notably through impairment in interleukin (IL)-22 productions. As intestinal defective IL-22 production was similarly observed in high fat diet (HFD)-fed mice, the inventors investigated the role of microbiota-derived AhR ligands in metabolic syndrome. They observed lower expression of Il22 and other related downstream genes, such as Reg3g and Reg3b, in the intestine of HFD-fed compared to control diet (CD)-fed mice (FIG. 1). Colon content of HFD-fed mice, displaying features of metabolic syndrome including insulin resistance and hepatic steatosis, showed significantly lower AhR activity, as assessed by a reporter system, consistent with reduced concentration of microbiota-derived AhR ligand indole acetic acid (IAA) and reduced tryptophan concentration in the colon mucosa compared to CD-fed mice (FIG. 7*a-b*, FIG. 8). Lower AhR activity was similarly observed in the colon content of rats fed with HFD and in murine model of genetically induced metabolic disorder (leptin-deficient, ob/ob mice) (FIG. 7*a*). In contrast, kynurenine, a tryptophan metabolite produced by host cell through indoleamine 2,3-dioxygenase 1, was significantly increased in HFD group (FIG. 7*c*), which is in accordance with the low-grade intestinal inflammation associated with HFD. Reduced AhR metabolic activity of HFD microbiota was associated with different profile compared to CD microbiota, which is reminiscent of previous reports showing that the microbiota of obese human and animals display higher Firmicutes and lower Bacteriodetes. Specifically, HFD microbiota had a relative increase in bacteria belonging to Lachnospiraceae and Clostridiaceae family while there was a lower abundance of bacteria from the Rikenellaceae as well as the Bifidobacteriaceae family compared to CD microbiota.

Figure 10:
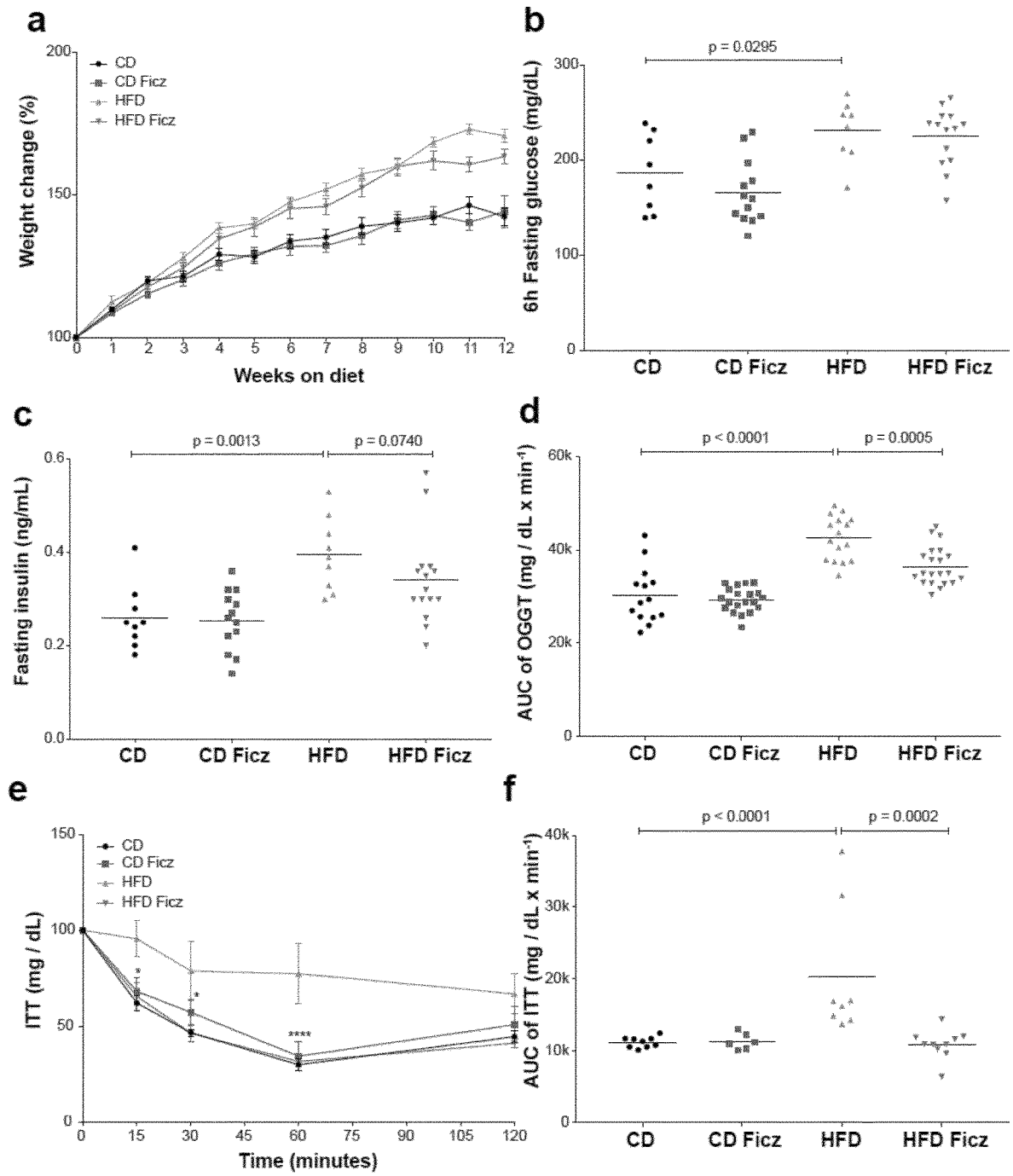
FIG. 10. Treatment with AhR agonist Ficz attenuated HFD-induced metabolic dysfunction. (a) Body weight gain (n=10/group). (b) Blood glucose and (c) insulin after 6 h of fasting. (d) Area under the curve (AUC) of OGGT. Refer to FIG. 9b for the OGGT figure. (e) Blood glucose level before and after insulin tolerance test (ITT; *$p<0.05$, n=6-10/group). (f) AUC of ITT. Concentration of (g) alanine transaminase (ALT), (h) aspartate transaminase (AST) and (i) total cholesterol from the serum of indicated mice. (j) Liver triglycerides after 6 h of food deprivation. Statistical comparison was performed by first testing normality using Kolmogorov-Smirnov test and then unpaired t-test or Mann-Whitney test.
Figure 11:
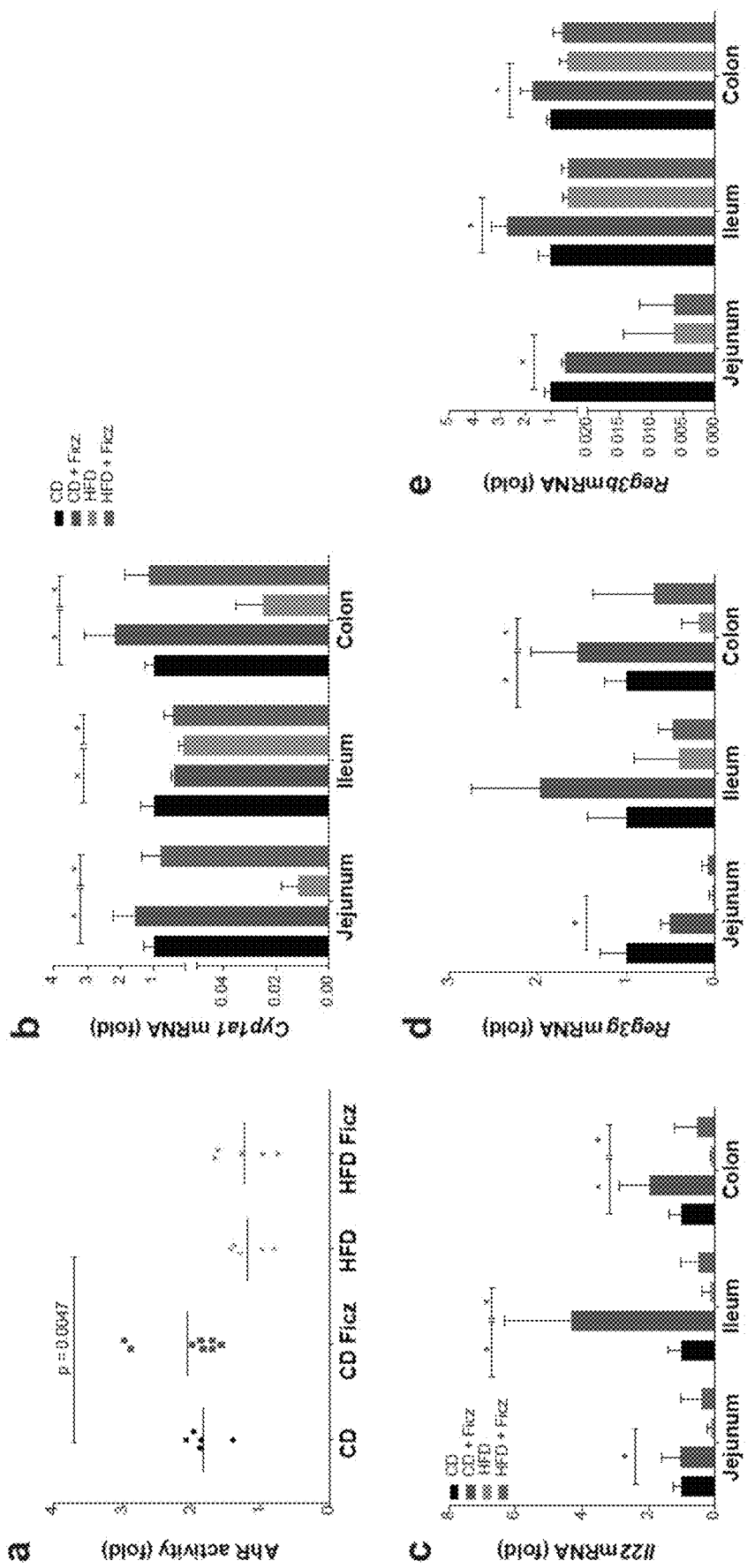
FIG. 11. Treatment with AhR agonist Ficz did not improve fecal AhR activity but attenuated HFD-associated defective intestinal AhR activation and Il22 expression. (a) AhR activity of stools from mice fed with CD or HFD for 12 weeks and treated with AhR agonist Ficz or vehicle. Transcript expression of (b) Cyp1a1 (c) Il22, (d) Reg3g and (e) Reg3b in different intestinal segments of indicated mice (n=5-12/group). Statistical comparison was performed by first testing normality using Kolmogorov-Smirnov test and then ANOVA or Kruskal-Wallis test with Bonferroni or Dunn's post hoc test.
Figure 12:
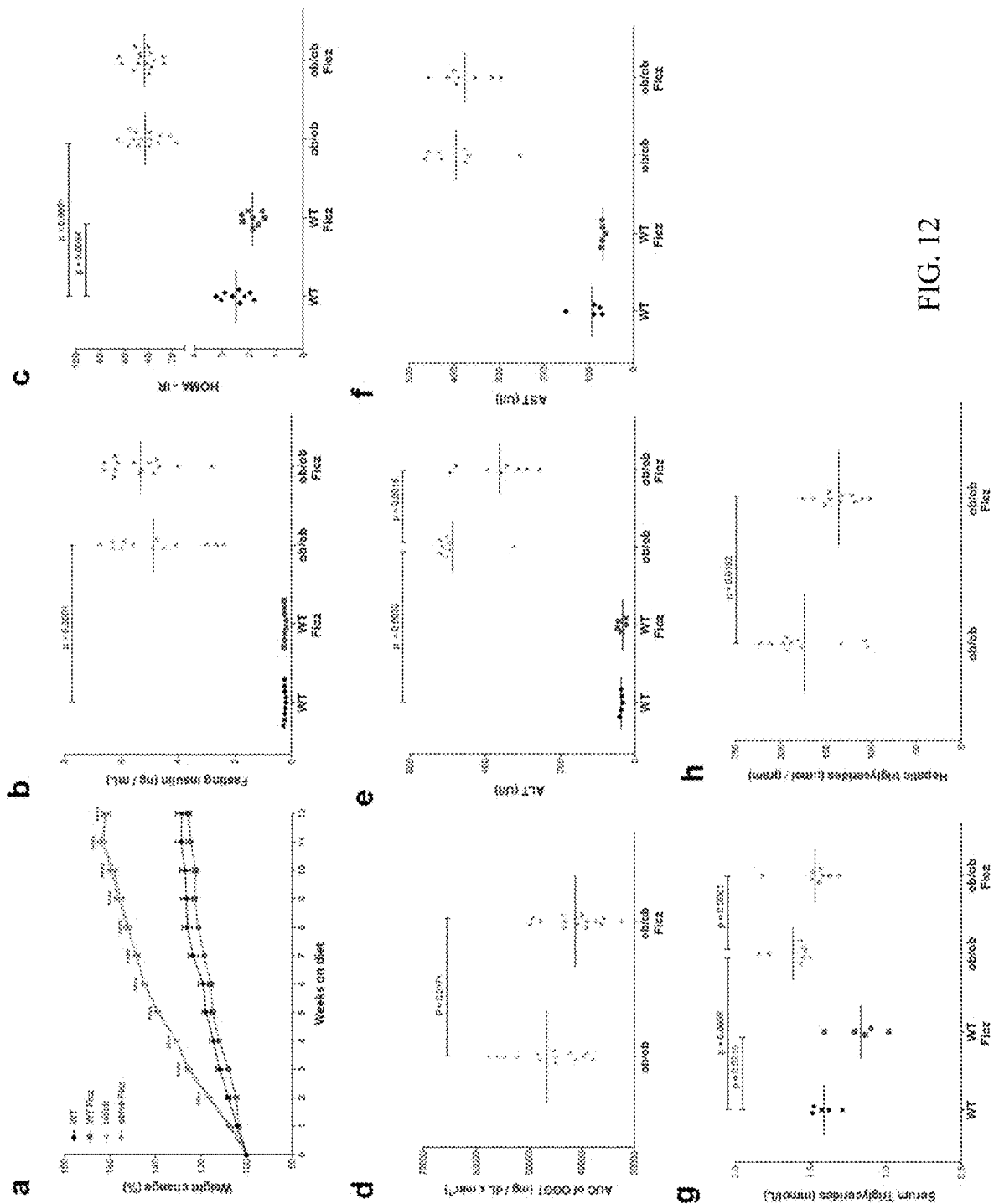
FIG. 12. Treatment with AhR agonist Ficz reduced features of metabolic syndrome in ob/ob mice. (a) Body weight gain (n=10-15/group). (b) Insulin and (c) homeostatic model assessment-insulin resistance (HOMA-IR) after 6 h of fasting. (d) Area under the curve (AUC) of OGGT. Refer to FIG. 9f for the OGGT figure. Concentration of (e) alanine transaminase (ALT), (f) aspartate transaminase (AST) and (g) triglycerides in the serum of indicated mice. (h) Liver triglycerides after 6 h of food deprivation. Statistical comparison was performed by first testing normality using Kolmogorov-Smirnov test and then unpaired t-test or Mann-Whitney test.
Figure 13:
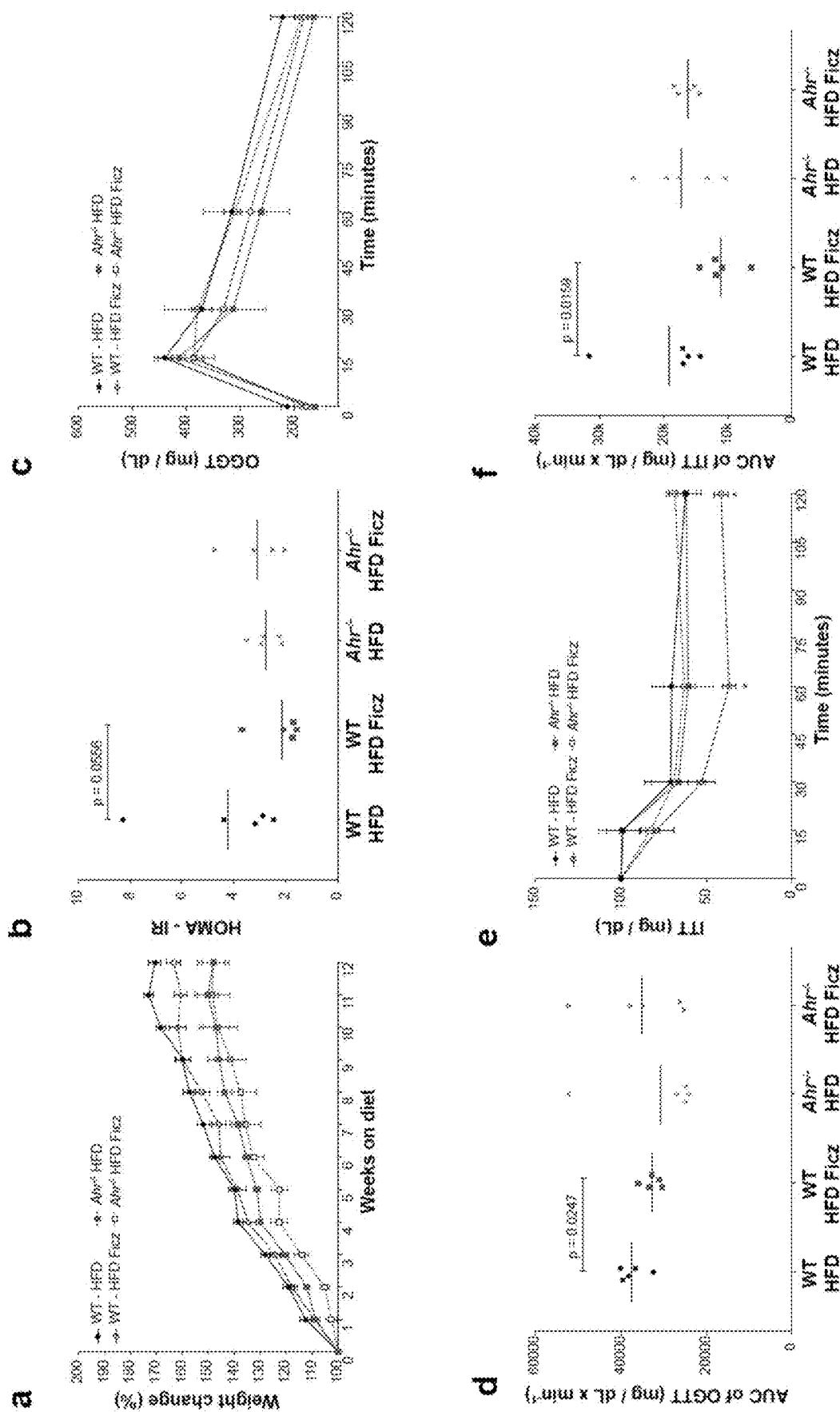
FIG. 13. Ficz treatment did not alleviate metabolic syndrome in AhR-mice. (a) Weight gain after 12 weeks of HFD. (b) Homeostatic model assessment-insulin resistance (HOMA-IR) after 6 h of fasting. (c) Blood glucose level before and after OGGT (n=10/group). (d) Area under the curve (AUC) of OGGT. (e) Blood glucose level before and after insulin tolerance test (ITT; n=10/group). (f) AUC of ITT. Statistical comparison was performed by first testing normality using Kolmogorov-Smirnov test and then unpaired t-test or Mann-Whitney test.
Figure 14:
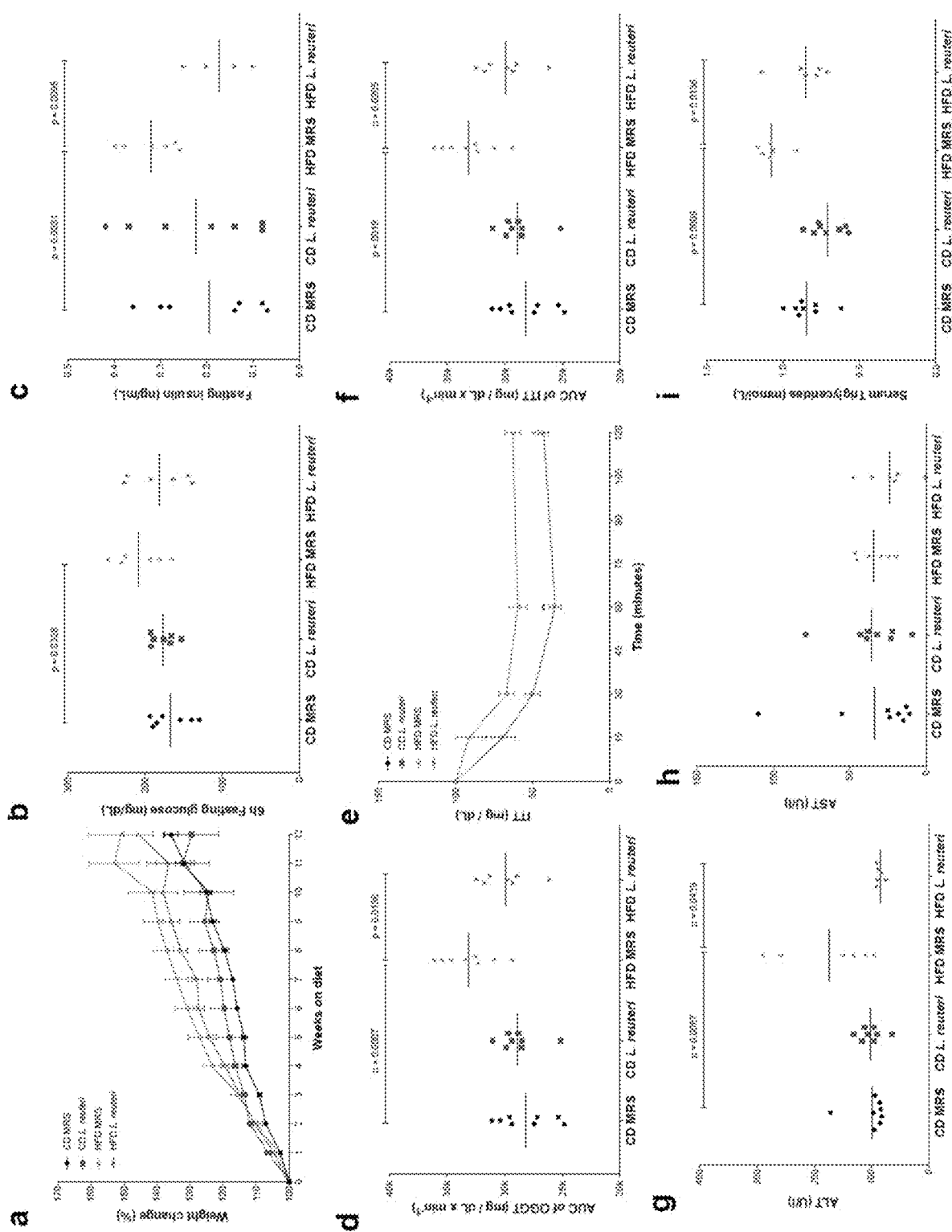
FIG. 14. Inoculation with high-producing AhR ligands bacteria attenuated HFD-induced metabolic syndrome. (a)

To investigate the physiological importance of impaired microbiota AhR activity, 6-formylindolo(3,2-b)carbazole (Ficz), an AhR agonist, was administered to HFD-fed mice. Ficz-treatment did not significantly affect weight gain, but it improved insulin resistance, as assessed by homeostatic model assessment method (HOMA-IR), in HFD group (FIG. 9*a*). HFD-fed mice also showed better glucose clearance during oral glucose tolerance test (OGGT), insulin sensitivity during insulin tolerance test (ITT) and features of non-alcoholic fatty liver disease, including lower hepatic triglycerides and lower serum concentration of liver-specific enzyme aspartate transaminase (AST) and cholesterol (FIG. 9*b-c*; FIG. 10). Ficz was not able to correct the impaired AhR agonist production of the microbiota but was sufficient to restore the intestinal expression of Il-22, Reg3g and Reg3b as well as Cyp1a1, which is a biomarker for AhR activation (FIG. 11), highlighting the efficacy of Ficz treatment to compensate for the reduced microbiota-specific AhR signaling. Moreover, Ficz treatment was able to reduce glucose dysmetabolism, hepatic dysfunctions and serum triglycerides in ob/ob mice (FIG. 9*e-h*, FIG. 12). The AhR-dependant mechanism of Ficz was confirmed by its lack of efficacy to treat metabolic syndrome in HFD-fed AhR−/− mice (FIG. 13).

The inventors next investigated whether administration of a previously isolated *Lactobacilllus reuteri* strain that exhibits natural high tryptophan-metabolic activity can similarly reverse the HFD-associated metabolic dysfunctions. *L. reuteri* supplementation was sufficient to rectify the impaired AhR activity of HFD-fed mice (FIG. 9*i*). Furthermore, *L. reuteri* administration recapitulated the improvements demonstrated by Ficz treatment, particularly in regards to glucose clearance, insulin sensitivity and serum lipid levels (FIG. 9*j-m*, FIG. 14); thus, underscoring that microbiota-specific AhR activation is instrumental in maintenance of metabolic homeostasis.

Intestinal barrier dysfunction and low-grade inflammation had been widely accepted as a distinctive feature of metabolic disorders. Leaky gut allows the passage of microbial products, such as lipopolysachharide (LPS), across mucosa leading to metabolic endotoxaemia, defined as moderate increase in plasma concentration of LPS, a phenotype often observed in humans and animals with metabolic syndrome and had been further shown to trigger the systemic inflammatory reaction driving metabolic disease. Indeed, subcutaneous infusion of LPS induces many features of metabolic diseases in wild-type mice but not in mice that lacks the LPS immune co-receptor CD14 and Toll-like receptor 4 knockout mice are resistant to metabolic dysfunctions. In light of these data, the inventors sought to determine whether AhR signaling activation has an impact on intestinal barrier function by evaluating permeability of different intestinal segments in Ussing chamber. Similar with previous studies showing barrier dysfunction in HFD-fed animals, the inventors observed that HFD-fed mice showed higher translocation of fluorescein-labeled LPS (F-LPS) as well as other permeability markers, Antonia-red-labeled dextran (ARD4) and fluorescein-labeled sulfonic acid (FS4), compared to CD group, particularly in the colon and jejunum. Ficz treatment was effective in reducing the barrier dysfunction in HFD mice (FIG. 15*a-c*). To confirm whether the barrier improvement was specific to Ficz signaling, they employed a reductionist system involving human intestinal epithelial cell line. Ficz stimulation was able to prevent TNF-α-associated decreased in trans-epithelial resistance (TER) and increased translocation of fluorescein-labeled dextran (FD4) in-vitro (FIG. 15*d-e*). Similar studies demonstrated the efficacy of Ficz in reversing hypoxia-driven intestinal barrier dysfunction and the importance of AhR ligands, especially bacterial derived indole metabolites, in regulating mucosal and epithelial barrier integrity. Thus, in conjunction with the present results, these data reinforce the beneficial effect of AhR signaling at epithelial cell level.

The inventors next determined the relevance of increased permeability in HFD-fed mice by measuring serum concentration of soluble CD14 (sCD14), which is released from monocytes upon LPS activation and thus can be used as a surrogate marker for systemic LPS availability. HFD-fed mice showed elevated levels of serum sCD14 compared to CD-fed mice, and Ficz treatment in HFD-fed mice significantly prevented this (FIG. 15*f*). In parallel, Ficz-treated HFD mice showed reduced systemic inflammatory markers, characterized by reduced TNF-α and IFN-γ production by splenic cells compared to non-treated mice (FIG. 15*g-h*), suggesting that reinforcing mucosal barrier may prevent metabolic syndrome associated endotoxemia and related systemic inflammation.

In addition to its role in stimulating IL-22 production and strengthening the integrity of intestinal mucosa, microbiota derived-indole derivatives had also been shown to be efficient in stimulating the secretion of the incretin hormone GLP-1 from intestinal enteroendocrine cells (EEC). GLP-1 has a myriad of metabolic functions including glucose homeostasis and liver function, and drugs that mimics GLP-1 action are now widely used in treatment of type-2 diabetes. The inventors observed significantly lower expression of intestinal proglucagon, a gene that encodes GLP-1, and decreased levels of total GLP-1 in the serum of HFD compared to CD-fed mice (FIG. 15$i$). Ficz treatment was able to correct intestinal mRNA expression of proglucagon and serum GLP-1 deficiency in HFD-fed mice, highlighting the physiological relevance of reduced indole ligands in metabolic syndrome (FIG. 15$j$). To explore the mechanism leading to correction of GLP-1 following treatment with AhR agonist, GLUTag cells, which is a murine EEC line that express the proglucagon gene and secretes GLP-127 as well as highly express AhR, was stimulated with Ficz. Ficz promoted strong GLP-1 secretion, comparable to when GLUTag cells were stimulated with Forskolin, a strong inducer of GLP-1 secretion that acts through G protein-coupled receptor. This effect was confirmed to be AhR specific as the response disappeared in the presence of AhR antagonist (FIG. 15$k$). Altogether, the results suggest a novel mechanism by which AhR signaling may contribute to the outcome of metabolic dysfunction.

Finally, the inventors explored whether their findings have human relevance by analyzing fecal samples from individuals with metabolic syndrome and from healthy subjects for their ability to activate AhR (Table 1 for subjects information). Fecal samples from obese individuals (body mass index, BMI >30) induced lower AhR activation compared non-obese individuals (FIG. 16$a$). Furthermore, AhR activity and BMI showed strong negative correlation (FIG. 16$b$). Individuals displaying metabolic risk factors, such as T2D and high blood pressure (HBP), similarly showed lower AhR activity (FIG. 16$c$-$d$, FIG. 17). Fecal samples of individuals with metabolic dysfunctions further displayed lower concentrations of gut microbiota-derived AhR agonists, including IAA (FIG. 16$e$-$h$, FIG. 18), conforming to the impaired stool AhR activity. In contrast, fecal kynurenine concentration was up-regulated in individuals with metabolic dysfunctions (FIG. 16$i$-$l$). Collectively, the clinical results support the relevance of the animal experiments findings.

TABLE 1

Clinical subjects information.

| | Whole population | Patients with metabolic syndrome | Healthy controls |
|---|---|---|---|
| n | 127 | 92 | 35 |
| Male gender (n, %) | 58 (45.7) | 43 (46.8) | 15 (42.9) |
| Age (mean, SD) | 51 (17) | 58 (14) | 35 (13) |
| BMI (mean, SD) | 29 (8) | 31 (8) | 23 (3) |
| BMI > 30 (n, %) | 38 (30) | 37 (40) | 1 (3) |
| High blood pressure (n, %) | 32 (25) | 32 (35) | 0 |
| Diabetes (n, %) | 17 (13) | 17 (18) | 0 |

Materials and Methods

Mice.

Male C57BL/6JRj mice and ob/ob mice on the C57BL/6JRj background were purchased from Janvier (France) and used after 1 week of receipt. AhR$^{-/-}$ on the C57BL/6JRj background and wild type mice were housed and bred at Saint Antoine Research Center. AhR$^{-/-}$ and C57BL/6JRj at 5 weeks of age were fed ad libitum with purified control diet (CD, Envigo MD.120508) or high fat diet (HFD, 18% milk-fat, Envigo MD.97222) for 12 weeks. Ob/ob and wild-type mice at 6-7 weeks of age were fed ad libitum with standard chow diet (R03, SAFE, Augy, France) for 12 weeks. 6 weeks old male Wistar were purchased from Janvier (France), used after 1 week of receipt and fed with either standard chow diet or HFD with 45% of energy from lipids and 17% of energy from sucrose. Animals were weighed weekly and weekly food consumption was measured cage-wise. Except when in-vivo permeability experiments were performed, all animals were fasted for 6 hours prior to sacrifice and then put to sleep using isoflurane. Animals were culled by cervical dislocation and appropriate tissues were harvested.

Animal Treatments.

For AhR agonist treatment, mice were injected i.p. with 6-formylindolo(3,2-b)carbazole (Ficz, Enzo Life Sciences, 1 μg/mouse) or vehicle (dimethyl sulfoxide, Sigma-Aldrich) once a week for 12 weeks. For treatment with bacteria with strong AhR activity, mice were gavaged daily with $10^9$ CFU of L. reuteri CNCM I-5022 or vehicle (MRS broth supplemented with 0.05% L-cysteine and 15% glycerol) for 12 weeks.

Measurement of AhR Activity.

AhR activity of human and animal stool samples was performed using a luciferase reporter assay method described previously (Lamas et al, 2016). Briefly, H1L1.1c2 cell line, containing dioxin-response element-driven firefly luciferase reporter plasmid pGudLuc1.1, was seeded in 96-well plate and then stimulated with human or animal stool samples for 24 h. Luciferase activity was measured using a luminometer and results were normalized based on the negative luciferase activity of the control.

Metabolites Measurement.

Concentration of metabolites from stool samples was quantified as previously described (Lamas et al, 2016). Briefly, L-tryptophan and L-kyrunenine were measured via HPLC using coluometric electrode assay (ESA Coultronics). Indole derivatives were quantified using liquid chromatography coupled to mass spectrometry using a Waters ACQUITY ultra performance liquid chromatography. Concentration of metabolites from stool samples was quantified as previously described (Lamas et al, 2016). Briefly, L-tryptophan and L-kyrunenine were measured via HPLC using coluometric electrode assay (ESA Coultronics). Indole derivatives were quantified using liquid chromatography coupled to mass spectrometry using a Waters ACQUITY ultra performance liquid chromatography (Garner et al, 2007).

16s rRNA Gene Sequencing.

16s rRNA gene sequencing of fecal DNA samples (collected at week 9 of CD or HFD) was performed as previously described (Lamas et al, 2016). Briefly, the V3-V4 region was amplified and sequencing was done using an Illumina MiSeq platform (GenoScreen, Lille, Fra). Raw paired-end reads were subjected to the following process: (1) quality-filtering using the PRINSEQ-lite PERL script by truncating the bases from the 3' end that did not exhibit a quality <30 based on the Phred algorithm; (2) paired-end read assembly using FLASH (fast length adjustment of short reads to improve genome assemblies) (Schmieder, R. & Edwards, R. Quality control and preprocessing of metagenomic datasets. Bioinformatics 27, 863-864 (2011)) with a minimum overlap of 30 bases and a 97% overlap identity; and (3) searching and removing both forward and reverse primer sequences using CutAdapt, with no mismatches allowed in the primers sequences. Assembled sequences for which perfect forward and reverse primers were not found were eliminated. Sequencing data were analyzed using the quantitative insights into microbial ecology (QIIME 1.9.1) software package. The sequences were assigned to OTUs using the UCLUST algorithm (Edgar, R. C. Search and clustering orders of magnitude faster than BLAST. Bioinformatics 26, 2460-2461 (2010).) with a 97% threshold of pairwise identity and classified taxonomically using the Greengenes reference database (McDonald, D. et al. An improved Greengenes taxonomy with explicit ranks for ecological and evolutionary analyses of bacteria and archea. *ISME J.* 6, 610-618 (2012).). Rarefaction was performed (13,000 sequences per sample) and used to compare abundance of OTUs across samples. Alpha-diversity was estimated using both richness and evenness indexes (Chao1, Shannon or number of observed species). Beta-diversity was measured by Bray Curtis distance matrix and was used to build Principal coordinates analysis (PCoA). Linear discriminant analysis (LDA) effect size (LEfSe) algorithm was used to identify taxa that are specific to diet and/or treatment (Segata, N. et al. Metagenomic biomarker discovery and explanation. Genome Biol. 12, R60 (2011).).

Oral Glucose Tolerance Test.

OGGT was performed 5-7 days before the sacrifice. Mice were fasted by removing the food and bedding 1 hour before the onset of light cycle. After 6 hours of fasting, glucose solution (2 g/kg for all mice except; 1 g/kg for ob/ob mice) was administered by oral gavage. Blood glucose level at time 0 (fasting glucose, taken before glucose gavage) and at 15, 30, 60 and 120 minutes after glucose gavage was analyzed using OneTouch glucometer (Roche). Glucose level was plotted against time and areas under the glucose curve (AUC) were calculated by following trapezoidal rule. Plasma insulin concentration (collected in EDTA-coated tubes) at time 0 (fasting insulin) and 30 was analyzed from tail vein blood (collected in EDTA-coated tubes) using ultra sensitive mouse insulin ELISA kit (Alpco). Homeostatic model assessment of insulin resistance (HOMA-IR) was calculated according to the formula: fasting glucose (nmol/L)×fasting insulin (microU/L)/22.5.

Intraperitoneal Insulin Tolerance Test.

ITT was performed 5-7 days before the sacrifice. Mice were fasted by removing the food and bedding 1 hour before the onset of light cycle. After 6 hours of fasting, insulin solution (0.5 U/kg) was administered intraperitoneally. Blood glucose level at time 0 (fasting glucose, taken before glucose gavage) and at 15, 30, 60 and 120 minutes after insulin challenge was analyzed using OneTouch glucometer (Roche). Glucose level was plotted against time and areas under the glucose curve (AUC) were calculated by following trapezoidal rule.

Measurements of Plasma Parameters.

Blood samples were collected in heparin-coated tubes via cardiac puncture, centrifuged and then plasma samples were stored at −80° C. until analysis. Plasma cholesterol, triglycerides, high-density lipoprotein (HDL), aspartate transaminase (AST) and alanine transaminase (ALT) measurement were performed by the Biochemistry Platform (CRI, UMR 1149, Paris) using Olympus AU400 Chemistry Analyzer.

Liver Histology and Hepatic Triglycerides Measurement.

A slice of left lobe of the liver was fixed in 4% PFA for 48 h and then transferred to ethanol, fixed in paraffin, trimmed, processed, sectioned into slices approximately 3 µm thick, mounted on a glass slide and stained with hematoxylin and eosin. Hepatic lipids were evaluated and quantified blindly using ImageJ software as previously described (Schneider et al, 2012; Crane et al, 2015).

In-Vivo Intestinal Permeability and Plasma sCD14 Measurement.

In-vivo assay of intestinal barrier function was performed using fluorescein-conjugated dextran (FITC-dextran, 4 kDA) method, as previously described (Laval et al, 2015). Briefly, on the day of sacrifice, FITC-dextran (0.6 mg/g of body weight) was administered to the mice by oral gavage and 3 h later, blood samples were collected in heparin-coated tubes. Fluorescence intensity was measured in the plasma using a microplate reader (Tecan). Plasma concentration of soluble CD14 (sCD14) was measured using CD14 ELISA kit (R&D) as per manufacturer's instructions.

Intestinal Permeability Measurement in Ussing Chambers.

Segments of colon, mid-jejunum and distal ileum were cut along the mesenteric border and mounted in Ussing chambers (Physiological instruments) exposing 0.2-0.3 cm$^2$ of tissue area to 2.5 mL of circulating oxygenated Kreb's Bicarbonate buffer containing 5 mM KCl, 114 mM NaCl, 2.15 mM $CaCl_2$, 1.10 mM $MgCl_2$, 25 mM $Na_2HCO_3$, 1.65 mM $Na_2HPO_4$ and 0.3 mM $NaH_2PO_4$, and maintained at 37° C. Additionally, glucose (10 mM) was added to the serosal buffer as a source of energy and osmotically balanced by mannitol (10 mM) in the mucosal buffer. Flourescein labeled lipopolysachharide (F-LPS; 80 µg/mL; Sigma-Aldrich) was used as a probe to assess macromolecular permeability. Additionally, Antonia-red labeled dextran (ARD4; 400 µg/mL; molecular weight, 4000 Da; TdB) and fluorescein-labeled sulfonic acid (FS4; 40 µg/mL; molecular weight, 400 Da; TdB) were simultaneously used to assess paracellular and transcellular permeability. All probes were added to the luminal buffer once equilibrium was reached (10-15 minutes after mounting the tissues in the chamber). Serosal samples (200 uL) were taken at 30 min intervals for 2 h and replaced with fresh buffer to maintain constant volume. Fluorescence intensity of the serosal samples was measured using a microplate reader (Tecan) and concentration of probes was calculated from a standard curve. The flux of probes from the mucosa to the serosa was calculated as the average value of two consecutive stable flux periods (60-90 and 90-120 min) and expressed as ng/$cm^2$/h.

Monolayer Preparation and TER Measurement.

Caco-2 cells were grown on Transwell semi permeable filter support (12 mm diameter wells, polystyrene membranes with 0.4 mm pores, Costar-Corning), plated at $1\times10^5$ cells per well and used 18-20 days after confluence. TER was measured at time 0 (TO), which is before adding Ficz (175 nM) onto both the apical and basal surface 3 h prior to cytokine stimulation and at the end of cytokine stimulation (time 36 h, T36). Cells were first stimulated with IFN-γ (10 ng/ml; R&D Systems) for 24 hours to promote expression of TNF-α receptors followed by stimulation with TNF-α (2.5 ng/ml; R&D Systems) for 12 hours. Cytokines were only added at the basal compartment without manipulating the apical compartment. Wells without Ficz and cytokines were used as controls. TER data was presented as a ratio: Ratio= (TER Treatment Time 36/TER Treatment TO)/(TER Control T36/TER Control TO). For flux of fluorescein isothiocyanate-labeled dextran (FD4; molecular weight, 4000 Da;

TdB), monolayers were washed after stimulation with Hanks' balanced salt solution (HBSS) and transferred to fresh HBSS. 1 mg/ml of fluorescein isothiocyanate-dextran was added to the apical layer and incubated at 37° C. Samples were removed from the basal chamber after 120 minutes. Fluorescence of basal samples was determined using a fluorescent plate reader (Tecan) and flux was calculated from a standard curve. Experiments were performed twice in triplicate or quadruplicate for a total of two independent experiments.

GLP-1 Secretion.

GLP-1 secretion was assessed by immunoassay from GLUTag (Drucker et al, 1994). Cells were plated in 24-well plates at $2 \times 10^5$ cells per well and cultured for 2-3 days. On the day of the experiment, cells were washed twice with Kreb's Ringer solution containing 30 mM KCl, 120 mM NaCl, 0.5 mM $CaCl_2$, 0.25 mM $MgCl_2$, and 2.2 mM $NaHCO_3$ supplemented with 0.5% (wt/vol) BSA. Cells were stimulated with Forskolin (10 µM; Sigma-Aldrich) or Ficz (175 nM; Enzo Pharmaceuticals) in the presence of absence of AhR antagonist CH223191 (10 µM; Sigma-Aldrich) or vehicle (DMSO) for 2 h in Kreb's Ringer solution. GLP-1 concentrations at time 0 h and 2 h were measured using a total GLP-1 Elisa kit (Millipore) as per manufacturer's instructions. GLP-1 concentrations were expressed as the difference at time 2 h and 0 h divided by total cell protein concentration. Experiments were performed twice in triplicate or quadruplicate for a total of two independent experiments.

Cytokines Quantification.

Single cell suspensions from MLN and spleen were isolated by smashing the cells in 70 µm mesh. $1 \times 10^6$ cells were plated in 24 well plate and then stimulated with phorbol 12-myristate 13-acetate (PMA, 50 ng/mL; Sigma-Aldrich) and ionomycin (1 uM; Sigma Aldrich) for 48 h at 37° C. Supernatants were collected and used for cytokine analysis. Cytokines were measured using individual ELISA kit (R&D Mouse DuoSet IL-6; Mabtech IFN-γ, IL-17a ELISA kits; Ebioscience TNF-α ELISA kit).

Gene Expression Analysis Using Quantitative Reverse-Transcription PCR.

Total RNA was isolated from different intestinal segments using RNeasy Mini Kit, according to manufacturer's instructions. Quantitative RT-PCR was performed using Biorad iScript cDNA Synthesis kit and then a Takyon SYBR Green PCR kit in a StepOnePlus apparatus (Applied Biosystems) with specific mouse oligonucleotides described previously (Lamas et al). qPCR data was analyzed using the $2^{-\Delta\Delta Ct}$ quantification method with mouse Gapdh as an endogenous control.

Metabolic Syndrome Cohort.

All individuals came from three cohorts of Paris Hospitals (Paris, France) and provided informed consent. All subjects did not receive antibiotics in the last three months before sampling. Approval for human studies was obtained from local ethics committees (Comite de Protection des Personnes Ile-de-France IV, IRB 00003835 Suivitheque study; registration number 2012/05NICB and Dispo cohort, registration number 2016/34 NICB; Comite de Protection des Personnes Ile-de-France III, Mabac cohort, registration number S.C. 3218).

Statistical Analysis.

In each experiment, multiple mice were analyzed as biological replicates. No statistical methods were used to predetermine sample size. Dot plots with a linear scale show the arithmetic mean. Bar graphs are expressed as mean±standard error of mean (SEM). Except for 16s rRNA results, GraphPad Prism version 7.0b was used for all statistical analysis. The Kolmogorov-Smirnov test was used to verify that all data set were normally distributed. For data sets that failed normality, nonparametric tests were used to analyze statistical differences. For comparisons between two groups, significance was determined using two-tailed Student's t-test or nonparametric Mann Whitney test. For comparisons among more than two groups, one way analysis of variance (ANOVA) followed by post-hoc Bonferroni test or nonparametric Kruskal Wallis test followed by post hoc Dunn's test and two-way ANOVA corrected for multiple comparison with a Bonferroni test were used. An F or Bartlett's test was performed to determine difference in variances for t-tests and ANOVAs, respectively. An unpaired Student's t-test with Welch's correction was applied when variances were not equal. Differences were noted as significant at p≤0.05.

Example 3

The inventors assayed the capacity of bacterial strains to produce AhR agonists (FIG. 19). Bacterial strains CNCM I-5019, CNCM I-5020, CNCM I-5021, CNCM I-5022, CNCM I-5023 are able to produce AhR agonists. In addition, other publicly available strains also show the same capacity.

Materials and Methods

Luciferase Assay.

The H1L1.1c2 cell line, containing a stably integrated dioxin-response element (DRE)-driven firefly luciferase reporter plasmid pGudLuc1.1, has been described previously[1,2]. The cells were seeded in 96-well plates at $7.5 \times 10_4$ cells/well in 100 µl of complete Dulbecco's modified Eagle's medium (DMEM) (with 10% heat-inactivated FCS, 50 IU/ml penicillin, and 50 µg/ml streptomycin; Sigma-Aldrich) and cultured (37° C., 10% $CO_2$) for 24 h before treatment. This cell line tested negative for *mycoplasma* contamination and was used in this study to determine AHR activity of bacterial samples.

Bacterial strains were grown in appropriate medium (MRS medium for Lactobacilli). Culture supernatants were stored at −80° C. until processing. To assess agonistic activity, the cells were treated with culture supernatants diluted to 2%, 10%, or 20% in complete DMEM. Controls consisted of cells treated with DMEM with bacterial culture medium as the negative control, or 0.2 µg/µl of 6-formylindolo[3,2-b]carbazole (FICZ; Sigma-Aldrich) diluted in DMEM as the positive control. After 24 h of incubation, wells were washed with 100 µl PBS, and 50 µl Promega lysis buffer was added to each well. The plates were shaken for 30 min to lyse the cells. After adding 100 µl of luciferase reagent (Promega), luciferase activity was measured using a luminometer. The results were normalized based on the negative luciferase activity of the control.

REFERENCE

Crane, et al. *Nat Med* 21, 166-172, doi:10.1038/nm.3766 (2015).

Drucker, et al. *Mol Endocrinol* 8, 1646-1655, doi:10.1210/mend.8.12.7535893 (1994).

Garner, et al. FASEB J 21, 1675-1688, doi:10.1096/fj.06-6927com (2007).

Lamas et al. Nat Med. 2016 June; 22(6):598-605. doi: 10.1038/nm.4102. Epub 2016 May 9. PubMed PMID: 27158904.

Kerley-Hamilton et al. Environ Health Perspect. 2012 September;120(9):1252-9. doi: 10.1289/ehp.1205003. Epub 2012 May 18. PubMed PMID: 22609946; PubMed Central PMCID: PMC3440132.

Laval, et al. *Gut microbes* 6, 1-9, doi:10.4161/19490976.2014.990784 (2015).

Schneider, et al. *Nat Methods* 9, 671-675 (2012).

Xu et al. Int J Obes (Lond). 2015 August; 39(8):1300-9. doi: 10.1038/ijo.2015.63. Epub 2015 Apr. 24. PubMed PMID: 25907315; PubMed Central PMCID: PMC4526411.

---

The invention claimed is:

1. A method for the treatment of metabolic syndrome and the associated disorders selected from the group consisting of cardiovascular disease, insulin resistance, glucose intolerance, type 2 diabetes, fatty liver disease, and lipodystrophy, in a subject comprising administering a bacterial probiotic that produces an aryl hydrocarbon receptor (AhR) agonist to a subject.

2. The method according to claim 1, wherein the cardiovascular disease is selected from the group consisting of coronary heart disease, heart attack and stroke.

3. The method according to claim 1, wherein the subject exhibits decreased AhR activity or decreased AhR activity of gut microbiota.

4. The method according to claim 1, wherein the AhR agonist is selected from the group consisting of indole derivatives, tryptophan catabolites of the microbiota, kynurenine, kynurenic acid, indole-3-aldehyde (IAld), tryptamine, indole 3-acetate, 3-indoxyl sulfate, 6-formylindolo (3,2-b)carbazole (FICZ), 2,3,7,8-tetrachlorodibenzo-p-dioxin (TCDD), tryptophan derivatives, flavonoids, biphenyls, AhR modulator (SAhRM), diindolylmethane (DIM), methyl-substituted diindolylmethanes, dihalo- and dialkylDIM analogs, mexiletine, polycyclic aromatic hydrocarbon (PAH), polychlorinated biphenyl (PCB), β-naphthoflavone (βNF), 5,6 benzoflavone (5,6 BZF), 3-indoxyl-sulfate (13 S), 1-(4-Methylphenyl)-2-(4,5,6,7-tetrahydro-2-imino-3 (2H)-benzothiazolyl)ethanone hydrobromide (Pifithrin-α hydrobromide), (2'Z,3'E)-6-Bromo-1-methylindirubin-3'-oxime (MeB 10), 5-hydroxy-7-methoxyflavone, 7-methoxyisoflavone, 6-methylflavone, 3-hydroxy-6-methylflavone, pinocembrin (5,7-dihydroxyflavanone) 7,8,2'-trihydroxyflavone and 1,4-dihydroxy-2-naphthoic acid (DHNA).

5. The method according to claim 1, wherein the bacterial probiotic is a bacterium naturally producing AhR agonist or a genetically modified bacterium producing an AhR agonist.

6. The method according to claim 5, wherein said bacterium is an *Allobaculum, Lactobacillus, Adlercreutzia*, Actinobacteria, lactic acid bacterium, *Streptococcus thermophilus, Bifidobacterium*, Propionic acid bacterium, *Bacteroides, Eubacterium*, anaerobic *Streptococcus, Anaerostipes* or *Enterococcus*.

7. The method according to claim 6, wherein the bacterial probiotic is an *Allobaculum*.

8. The method according to claim 6, wherein the bacterial probiotic is a *Lactobacillus*.

9. The method according to claim 8, wherein the bacterial probiotic is selected from the group consisting of *Lactobacillus reuteri, Lactobacillus taiwanensis, Lactobacillus animalis, Lactobacillus murinus, Lactobacillus salivarius, Lactobacillus gasseri, Lactobacillus bulgaricus*, and *Lactobacillus delbrueckii* subsp. *Bulgaricus*.

10. The method according to claim 5, wherein said bacterium is *Allobaculum stercoricanis, Lactobacillus reuteri, Lactobacillus taiwanensis, Lactobacillus johnsonii, Lactobacillus animalis, Lactobacillus murinus, Lactobacillus salivarius, Lactobacillus gasseri, Lactobacillus bulgaricus, Lactobacillus delbrueckii* subsp. *Bulgaricus, Streptococcus thermophilus, Anaerostipes hadrus, Anaerostipes caccae, Anaerostipes butyraticus, Ruminococcus gnavus, Faecalibacterium prausnitzii* or *Escherichia coli*.

11. The method according to claim 5, wherein the bacterial probiotic is *Lactobacillus delbrueckii* subsp. *Bulgaricus* or is *Lactobacillus delbrueckii* subsp. *Bulgaricus* OLL1181.

12. The method according to claim 1, wherein the bacterial probiotic is selected from the group consisting of bacterial probiotics available under CNCM deposit numbers CNCM I-5019, CNCM I-5020, CNCM I-5021, CNCM I-5022, CNCM I-5023 and any combination thereof.

13. The method according to claim 1, wherein the bacterial probiotic is administered orally or rectally.

14. The method according to claim 1, wherein said method reduces weight gain of the subject.

15. The method according to claim 1, wherein said method improves glucose tolerance and insulin sensitivity in the subject.

16. The method according to claim 1, wherein the fatty liver disease is selected from the group consisting of non-alcoholic fatty liver disease and non-alcoholic steatohepatitis.

* * * * *

UNITED STATES PATENT AND TRADEMARK OFFICE
CERTIFICATE OF CORRECTION

PATENT NO. : 11,596,657 B2
APPLICATION NO. : 16/337951
DATED : March 7, 2023
INVENTOR(S) : Harry Sokol et al.

It is certified that error appears in the above-identified patent and that said Letters Patent is hereby corrected as shown below:

On the Title Page

(71) Applicants,
"INSTITUT NATIONAL DE LA RECHERCHE AGRONOMIQUE" should read --INSTITUT NATIONAL DE RECHERCHE POUR L'AGRICULTURE, L'ALIMENTATION ET L'ENVIRONNEMENT--.

(73) Assignees,
"INSTITUT NATIONAL DE LA RECHERCHE AGRONOMIQUE" should read --INSTITUT NATIONAL DE RECHERCHE POUR L'AGRICULTURE, L'ALIMENTATION ET L'ENVIRONNEMENT--.

In the Specification

Column 8,
Line 10, "(3NF)" should read --(βNF)--.

Column 16,
Line 57, "AhR-mice" should read --$AhR^{-/-}$ mice--.

Column 20,
Line 47, "(1 laM;" should read --(1 µM;--.

Signed and Sealed this
Fifth Day of September, 2023

Katherine Kelly Vidal
*Director of the United States Patent and Trademark Office*

SEQUENCE LISTING

```
<160> NUMBER OF SEQ ID NOS: 8

<210> SEQ ID NO 1
<211> LENGTH: 20
<212> TYPE: DNA
<213> ORGANISM: artificial sequence
<220> FEATURE:
<223> OTHER INFORMATION: primer

<400> SEQUENCE: 1
aactttggca ttgtggaagg                                                  20

<210> SEQ ID NO 2
<211> LENGTH: 20
<212> TYPE: DNA
<213> ORGANISM: artificial sequence
<220> FEATURE:
<223> OTHER INFORMATION: primer

<400> SEQUENCE: 2
acacattggg ggtaggaaca                                                  20

<210> SEQ ID NO 3
<211> LENGTH: 20
<212> TYPE: DNA
<213> ORGANISM: artificial sequence
<220> FEATURE:
<223> OTHER INFORMATION: primer

<400> SEQUENCE: 3
catgcaggag gtggtacctt                                                  20

<210> SEQ ID NO 4
<211> LENGTH: 20
<212> TYPE: DNA
<213> ORGANISM: artificial sequence
<220> FEATURE:
<223> OTHER INFORMATION: primer

<400> SEQUENCE: 4
cagacgcaag catttctcag                                                  20

<210> SEQ ID NO 5
<211> LENGTH: 22
<212> TYPE: DNA
<213> ORGANISM: artificial sequence
<220> FEATURE:
<223> OTHER INFORMATION: primer

<400> SEQUENCE: 5
ttcctgtcct ccatgatcaa aa                                               22

<210> SEQ ID NO 6
<211> LENGTH: 21
<212> TYPE: DNA
<213> ORGANISM: artificial sequence
```

```
<220> FEATURE:
<223> OTHER INFORMATION: primer

<400> SEQUENCE: 6
catccacctc tgttgggttc a                                      21

<210> SEQ ID NO 7
<211> LENGTH: 21
<212> TYPE: DNA
<213> ORGANISM: artificial sequence
<220> FEATURE:
<223> OTHER INFORMATION: primer

<400> SEQUENCE: 7
atgctgctct cctgcctgat g                                      21

<210> SEQ ID NO 8
<211> LENGTH: 24
<212> TYPE: DNA
<213> ORGANISM: artificial sequence
<220> FEATURE:
<223> OTHER INFORMATION: primer

<400> SEQUENCE: 8
ctaatgcgtg cggagggtat attc                                   24
```